(12) United States Patent
Raney et al.

(10) Patent No.: US 10,478,534 B2
(45) Date of Patent: Nov. 19, 2019

(54) AUTOMATICALLY SWITCHING DIFFERENT ASPIRATION LEVELS AND/OR PUMPS TO AN OCULAR PROBE

(71) Applicant: Abbott Medical Optics Inc., Santa Ana, CA (US)

(72) Inventors: Robert G. Raney, Clyde Hill, WA (US); Michael J. Claus, Lakewood Ranch, FL (US); James Gerg, Lake Forest, CA (US); Wayne S. Wong, Irvine, CA (US); David A. King, Pleasanton, CA (US); James W. Staggs, Laguna Niguel, CA (US); Fred Lee, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 145 days.

(21) Appl. No.: 15/430,352

(22) Filed: Feb. 10, 2017

(65) Prior Publication Data

US 2017/0151090 A1 Jun. 1, 2017

Related U.S. Application Data

(62) Division of application No. 12/614,093, filed on Nov. 6, 2009, now Pat. No. 9,566,188.
(Continued)

(51) Int. Cl.
*A61M 1/00* (2006.01)
*A61F 9/007* (2006.01)

(52) U.S. Cl.
CPC ....... *A61M 1/0064* (2013.01); *A61F 9/00736* (2013.01); *A61F 9/00745* (2013.01);
(Continued)

(58) Field of Classification Search
CPC .............. A61M 1/0031; A61M 1/0037; A61M 1/0039; A61M 1/0058; A61M 1/0062;
(Continued)

(56) References Cited

U.S. PATENT DOCUMENTS 1,848,024 A 3/1932 Owen
2,123,781 A 7/1938 Huber
(Continued)

FOREIGN PATENT DOCUMENTS

AU 2006235983 A1 5/2007
EP 56019 A1 7/1982
(Continued)

OTHER PUBLICATIONS

Co-pending U.S. Appl. No. 13/922,475, filed Jun. 20, 2013.
(Continued)

*Primary Examiner* — Bhisma Mehta
*Assistant Examiner* — Larry R. Wilson
(74) *Attorney, Agent, or Firm* — Johnson & Johnson Surgical Vision, Inc.

(57) ABSTRACT

Methods and apparatuses for automatically switching different aspiration levels to an ocular probe are disclosed herein. The probe may be a phacoemulsification probe. A first aspiration level, supplied by a first pump, may be applied to the probe simultaneously with ultrasonic energy. A second aspiration level, supplied by a second pump, may be automatically switched from the first aspiration level. Control feed back of the pumps may be varied according to set thresholds.

10 Claims, 15 Drawing Sheets

Related U.S. Application Data

(60) Provisional application No. 61/198,626, filed on Nov. 7, 2008.

(52) U.S. Cl.
CPC ....... *A61F 9/00754* (2013.01); *A61M 1/0031* (2013.01); *A61M 1/0037* (2013.01); *A61M 1/0039* (2013.01); *A61M 1/0058* (2013.01); *A61M 1/0062* (2013.01); *A61M 1/0066* (2013.01); *A61M 1/0076* (2013.01); *A61M 2205/3331* (2013.01); *A61M 2205/50* (2013.01); *A61M 2210/0612* (2013.01); *A61M 2210/0618* (2013.01)

(58) Field of Classification Search
CPC .. A61M 1/0064; A61M 1/066; A61M 1/0076; A61M 3/02; A61M 3/0233; A61M 3/0237; A61M 3/0241; A61M 2205/3331; A61M 2205/50; A61M 2210/0612; A61M 2210/0618; A61M 1/0041–1/0047; A61F 9/00736; A61F 9/00745; A61F 9/00754; A61F 9/007; F04B 23/04; F04B 23/08; F04B 41/06; F04B 49/00

See application file for complete search history.

(56) References Cited

U.S. PATENT DOCUMENTS

| | | |
|---|---|---|
| 2,990,616 A | 7/1961 | Balamuth et al. |
| 3,076,904 A | 2/1963 | Claus et al. |
| 3,116,697 A | 1/1964 | Theodore |
| 3,439,680 A | 4/1969 | Thomas, Jr. |
| 3,526,219 A | 9/1970 | Lewis |
| 3,781,142 A | 12/1973 | Zweig |
| 3,857,387 A | 12/1974 | Shock |
| 4,017,828 A | 4/1977 | Watanabe et al. |
| 4,037,491 A | 7/1977 | Newbold |
| 4,189,286 A | 2/1980 | Murry et al. |
| 4,193,004 A | 3/1980 | Lobdell et al. |
| 4,247,784 A | 1/1981 | Henry |
| 4,276,023 A | 6/1981 | Phillips et al. |
| 4,286,464 A | 9/1981 | Tauber et al. |
| 4,537,561 A | 8/1985 | Xanthopoulos |
| 4,564,342 A | 1/1986 | Weber et al. |
| 4,590,934 A | 5/1986 | Malis et al. |
| 4,662,829 A | 5/1987 | Nehring |
| 4,665,621 A | 5/1987 | Ackerman et al. |
| 4,706,687 A | 11/1987 | Rogers et al. |
| 4,713,051 A | 12/1987 | Steppe et al. |
| 4,757,814 A | 7/1988 | Wang et al. |
| 4,758,220 A | 7/1988 | Sundblom et al. |
| 4,758,238 A | 7/1988 | Sundblom et al. |
| 4,772,263 A | 9/1988 | Dorman et al. |
| 4,773,897 A | 9/1988 | Scheller et al. |
| 4,818,186 A | 4/1989 | Pastrone et al. |
| 4,819,317 A | 4/1989 | Bauer et al. |
| 4,837,857 A | 6/1989 | Scheller et al. |
| 4,920,336 A | 4/1990 | Meijer |
| 4,921,477 A | 5/1990 | Davis |
| 4,925,444 A | 5/1990 | Orkin et al. |
| 4,933,843 A | 6/1990 | Scheller et al. |
| 4,941,518 A | 7/1990 | Williams et al. |
| 4,954,960 A | 9/1990 | Lo et al. |
| 4,961,424 A | 10/1990 | Kubota et al. |
| 4,965,417 A | 10/1990 | Massie |
| 4,983,901 A | 1/1991 | Lehmer |
| 4,998,972 A | 3/1991 | Chin et al. |
| 5,006,110 A | 4/1991 | Garrison et al. |
| 5,020,535 A | 6/1991 | Parker et al. |
| 5,026,387 A | 6/1991 | Thomas |
| 5,032,939 A | 7/1991 | Mihara et al. |
| 5,039,973 A | 8/1991 | Carballo |
| 5,091,656 A | 2/1992 | Gahn |
| 5,108,367 A | 4/1992 | Epstein et al. |
| 5,110,270 A | 5/1992 | Morrick |
| 5,125,891 A | 6/1992 | Hossain et al. |
| 5,160,317 A | 11/1992 | Costin |
| 5,195,960 A | 3/1993 | Hossain et al. |
| 5,195,961 A | 3/1993 | Takahashi et al. |
| 5,195,971 A | 3/1993 | Sirhan |
| 5,230,614 A | 7/1993 | Zanger et al. |
| 5,242,404 A | 9/1993 | Conley et al. |
| 5,249,121 A | 9/1993 | Baum et al. |
| 5,267,956 A | 12/1993 | Beuchat |
| 5,268,624 A | 12/1993 | Zanger |
| 5,271,379 A | 12/1993 | Phan et al. |
| 5,282,787 A | 2/1994 | Wortrich |
| 5,323,543 A | 6/1994 | Steen et al. |
| 5,342,293 A | 8/1994 | Zanger |
| 5,350,357 A | 9/1994 | Kamen et al. |
| 5,351,676 A | 10/1994 | Putman |
| 5,354,268 A | 10/1994 | Peterson et al. |
| 5,378,126 A | 1/1995 | Abrahamson et al. |
| 5,388,569 A | 2/1995 | Kepley |
| 5,429,601 A | 7/1995 | Conley et al. |
| 5,454,783 A | 10/1995 | Grieshaber et al. |
| 5,464,391 A | 11/1995 | Devale |
| 5,470,211 A | 11/1995 | Knott et al. |
| 5,470,312 A | 11/1995 | Zanger et al. |
| 5,499,969 A | 3/1996 | Beuchat et al. |
| 5,520,652 A | 5/1996 | Peterson |
| 5,533,976 A | 7/1996 | Zaleski et al. |
| 5,549,461 A | 8/1996 | Newland |
| 5,554,894 A | 9/1996 | Sepielli |
| 5,561,575 A | 10/1996 | Eways |
| 5,569,188 A | 10/1996 | Mackool |
| 5,580,347 A | 12/1996 | Reimels |
| 5,591,127 A | 1/1997 | Barwick et al. |
| 5,653,887 A | 8/1997 | Wahl et al. |
| 5,657,000 A | 8/1997 | Ellingboe |
| 5,676,530 A | 10/1997 | Nazarifar |
| 5,676,649 A | 10/1997 | Boukhny et al. |
| 5,676,650 A | 10/1997 | Grieshaber et al. |
| 5,693,020 A | 12/1997 | Rauh |
| 5,697,898 A | 12/1997 | Devine |
| 5,697,910 A | 12/1997 | Cole et al. |
| 5,700,240 A | 12/1997 | Barwick, Jr. et al. |
| 5,724,264 A | 3/1998 | Rosenberg et al. |
| 5,728,130 A | 3/1998 | Ishikawa et al. |
| 5,733,256 A | 3/1998 | Costin |
| 5,733,263 A | 3/1998 | Wheatman |
| 5,745,647 A | 4/1998 | Krause |
| 5,746,713 A | 5/1998 | Hood et al. |
| 5,747,824 A | 5/1998 | Jung et al. |
| 5,777,602 A | 7/1998 | Schaller et al. |
| 5,805,998 A | 9/1998 | Kodama |
| 5,807,075 A | 9/1998 | Jacobsen et al. |
| 5,810,765 A | 9/1998 | Oda |
| 5,810,766 A | 9/1998 | Barnitz et al. |
| 5,830,176 A | 11/1998 | Mackool |
| 5,843,109 A | 12/1998 | Mehta et al. |
| 5,859,642 A | 1/1999 | Jones |
| 5,871,492 A | 2/1999 | Sorensen |
| 5,879,298 A | 3/1999 | Drobnitzky et al. |
| 5,883,615 A | 3/1999 | Fago et al. |
| 5,899,674 A | 5/1999 | Jung et al. |
| 5,928,257 A | 7/1999 | Kablik et al. |
| 5,938,655 A | 8/1999 | Bisch et al. |
| 5,983,749 A | 11/1999 | Holtorf |
| 6,002,484 A | 12/1999 | Rozema et al. |
| 6,024,428 A | 2/2000 | Uchikata |
| 6,028,387 A | 2/2000 | Boukhny |
| 6,062,829 A | 5/2000 | Ognier |
| 6,077,285 A | 6/2000 | Boukhny |
| 6,086,598 A | 7/2000 | Appelbaum et al. |
| 6,109,895 A | 8/2000 | Ray et al. |
| 6,117,126 A | 9/2000 | Appelbaum et al. |
| 6,139,320 A | 10/2000 | Hahn |
| 6,150,623 A | 11/2000 | Chen |
| 6,159,175 A | 12/2000 | Strukel et al. |
| 6,179,829 B1 | 1/2001 | Bisch et al. |
| 6,200,287 B1 | 3/2001 | Keller et al. |

(56) References Cited

U.S. PATENT DOCUMENTS

| | | |
|---|---|---|
| 6,219,032 B1 | 4/2001 | Rosenberg et al. |
| 6,251,113 B1 | 6/2001 | Appelbaum et al. |
| 6,258,111 B1 | 7/2001 | Ross et al. |
| 6,260,434 B1 | 7/2001 | Holtorf |
| 6,360,630 B2 | 3/2002 | Holtorf |
| 6,368,269 B1 | 4/2002 | Lane |
| 6,411,062 B1 | 6/2002 | Baranowski et al. |
| 6,424,124 B2 | 7/2002 | Ichihara et al. |
| 6,436,072 B1 | 8/2002 | Kullas et al. |
| 6,452,120 B1 | 9/2002 | Chen |
| 6,452,123 B1 | 9/2002 | Chen |
| 6,491,661 B1 | 12/2002 | Boukhny et al. |
| 6,511,454 B1 | 1/2003 | Nakao et al. |
| 6,537,445 B2 | 3/2003 | Muller |
| 6,561,999 B1 | 5/2003 | Nazarifar et al. |
| 6,595,948 B2 | 7/2003 | Suzuki et al. |
| 6,632,214 B2 | 10/2003 | Morgan et al. |
| 6,674,030 B2 | 1/2004 | Chen et al. |
| 6,780,166 B2 | 8/2004 | Kanda et al. |
| 6,830,555 B2 | 12/2004 | Rockley et al. |
| 6,852,092 B2 | 2/2005 | Kadziauskas et al. |
| 6,862,951 B2 | 3/2005 | Peterson et al. |
| 6,908,451 B2 | 6/2005 | Brody et al. |
| 6,962,488 B2 | 11/2005 | Davis et al. |
| 6,962,581 B2 | 11/2005 | Thoe |
| 6,986,753 B2 | 1/2006 | Bui |
| 7,011,761 B2 | 3/2006 | Muller |
| 7,012,203 B2 | 3/2006 | Hanson et al. |
| 7,070,578 B2 | 7/2006 | Leukanech et al. |
| 7,073,083 B2 | 7/2006 | Litwin, Jr. et al. |
| 7,087,049 B2 | 8/2006 | Nowlin et al. |
| 7,103,344 B2 | 9/2006 | Menard |
| 7,167,723 B2 | 1/2007 | Zhang |
| 7,169,123 B2 | 1/2007 | Kadziauskas et al. |
| 7,236,766 B2 | 6/2007 | Freeburg |
| 7,236,809 B2 | 6/2007 | Fischedick et al. |
| 7,242,765 B2 | 7/2007 | Hairston |
| 7,244,240 B2 | 7/2007 | Nazarifar et al. |
| 7,289,825 B2 | 10/2007 | Fors et al. |
| 7,300,264 B2 | 11/2007 | Souza |
| 7,316,664 B2 | 1/2008 | Kadziauskas et al. |
| 7,336,976 B2 | 2/2008 | Ito |
| 7,381,917 B2 | 6/2008 | Dacquay et al. |
| 7,439,463 B2 | 10/2008 | Brenner et al. |
| 7,465,285 B2 | 12/2008 | Hutchinson et al. |
| 7,470,277 B2 | 12/2008 | Finlay et al. |
| 7,526,038 B2 | 4/2009 | McNamara |
| 7,572,242 B2 | 8/2009 | Boukhny |
| 7,591,639 B2 | 9/2009 | Kent |
| 7,731,484 B2 | 6/2010 | Yamamoto et al. |
| 7,776,006 B2 | 8/2010 | Childers et al. |
| 7,785,316 B2 * | 8/2010 | Claus .................. A61F 9/00745 604/118 |
| 7,811,255 B2 | 10/2010 | Boukhny et al. |
| 7,883,521 B2 | 2/2011 | Rockley et al. |
| 7,921,017 B2 | 4/2011 | Claus et al. |
| 7,967,777 B2 | 6/2011 | Edwards et al. |
| 8,070,712 B2 | 12/2011 | Muri et al. |
| 8,075,468 B2 | 12/2011 | Min et al. |
| 8,157,792 B2 | 4/2012 | Dolliver et al. |
| 9,033,940 B2 | 5/2015 | Muri et al. |
| 9,658,468 B2 | 5/2017 | Dai |
| 2001/0023331 A1 | 9/2001 | Kanda et al. |
| 2001/0047166 A1 | 11/2001 | Wuchinich |
| 2001/0051788 A1 | 12/2001 | Paukovits et al. |
| 2002/0004657 A1 | 1/2002 | Morgan et al. |
| 2002/0007671 A1 | 1/2002 | Lavi et al. |
| 2002/0019215 A1 | 2/2002 | Romans |
| 2002/0019607 A1 | 2/2002 | Bui |
| 2002/0045887 A1 | 4/2002 | Dehoogh et al. |
| 2002/0070840 A1 | 6/2002 | Fischer et al. |
| 2002/0098859 A1 | 7/2002 | Murata |
| 2002/0137007 A1 | 9/2002 | Beerstecher |
| 2002/0179462 A1 | 12/2002 | Silvers |
| 2002/0183693 A1 | 12/2002 | Peterson et al. |
| 2003/0028091 A1 | 2/2003 | Simon et al. |
| 2003/0028141 A1 | 2/2003 | Kadziauskas et al. |
| 2003/0047434 A1 | 3/2003 | Hanson et al. |
| 2003/0050619 A1 | 3/2003 | Mooijman et al. |
| 2003/0073980 A1 | 4/2003 | Finlay et al. |
| 2003/0083016 A1 | 5/2003 | Evans et al. |
| 2003/0108429 A1 * | 6/2003 | Angelini ............. A61M 1/0058 417/3 |
| 2003/0125717 A1 | 7/2003 | Whitman |
| 2003/0224729 A1 | 12/2003 | Arnold |
| 2003/0226091 A1 | 12/2003 | Platenberg et al. |
| 2004/0019313 A1 | 1/2004 | Childers et al. |
| 2004/0035242 A1 | 2/2004 | Peterson et al. |
| 2004/0037724 A1 | 2/2004 | Haser et al. |
| 2004/0068300 A1 | 4/2004 | Kadziauskas et al. |
| 2004/0092922 A1 | 5/2004 | Kadziauskas et al. |
| 2004/0097868 A1 | 5/2004 | Kadziauskas et al. |
| 2004/0127840 A1 | 7/2004 | Gara et al. |
| 2004/0193182 A1 | 9/2004 | Yaguchi et al. |
| 2004/0212344 A1 | 10/2004 | Tamura et al. |
| 2004/0215127 A1 | 10/2004 | Kadziauskas et al. |
| 2004/0224641 A1 | 11/2004 | Sinn |
| 2004/0253129 A1 | 12/2004 | Sorensen et al. |
| 2004/0267136 A1 | 12/2004 | Yaguchi et al. |
| 2005/0039567 A1 | 2/2005 | Peterson et al. |
| 2005/0054971 A1 | 3/2005 | Steen et al. |
| 2005/0065462 A1 | 3/2005 | Nazarifar et al. |
| 2005/0069419 A1 | 3/2005 | Cull et al. |
| 2005/0070859 A1 | 3/2005 | Cull et al. |
| 2005/0070871 A1 | 3/2005 | Lawton et al. |
| 2005/0095153 A1 | 5/2005 | Demers et al. |
| 2005/0103607 A1 | 5/2005 | Mezhinsky |
| 2005/0109595 A1 | 5/2005 | Mezhinsky et al. |
| 2005/0118048 A1 | 6/2005 | Traxinger |
| 2005/0119679 A1 | 6/2005 | Rabiner et al. |
| 2005/0130098 A1 | 6/2005 | Warner |
| 2005/0187513 A1 | 8/2005 | Rabiner et al. |
| 2005/0197131 A1 | 9/2005 | Ikegami |
| 2005/0209552 A1 | 9/2005 | Beck et al. |
| 2005/0209560 A1 | 9/2005 | Boukhny et al. |
| 2005/0228266 A1 | 10/2005 | McCombs |
| 2005/0236936 A1 | 10/2005 | Shiv et al. |
| 2005/0245888 A1 | 11/2005 | Cull |
| 2005/0261628 A1 | 11/2005 | Boukhny et al. |
| 2005/0267504 A1 | 12/2005 | Boukhny et al. |
| 2006/0035585 A1 | 2/2006 | Washiro |
| 2006/0036180 A1 | 2/2006 | Boukhny et al. |
| 2006/0041220 A1 | 2/2006 | Boukhny et al. |
| 2006/0046659 A1 | 3/2006 | Haartsen et al. |
| 2006/0074405 A1 | 4/2006 | Malackowski et al. |
| 2006/0078448 A1 | 4/2006 | Holden |
| 2006/0114175 A1 | 6/2006 | Boukhny |
| 2006/0145540 A1 | 7/2006 | Mezhinsky |
| 2006/0219049 A1 | 10/2006 | Horvath et al. |
| 2006/0219962 A1 | 10/2006 | Dancs et al. |
| 2006/0224107 A1 | 10/2006 | Claus et al. |
| 2006/0236242 A1 | 10/2006 | Boukhny et al. |
| 2007/0016174 A1 | 1/2007 | Millman et al. |
| 2007/0049898 A1 | 3/2007 | Hopkins et al. |
| 2007/0060926 A1 | 3/2007 | Escaf |
| 2007/0073214 A1 | 3/2007 | Dacquay et al. |
| 2007/0073309 A1 | 3/2007 | Kadziauskas et al. |
| 2007/0078379 A1 | 4/2007 | Boukhny et al. |
| 2007/0085611 A1 | 4/2007 | Gerry et al. |
| 2007/0107490 A1 | 5/2007 | Artsyukhovich et al. |
| 2007/0231205 A1 | 10/2007 | Williams et al. |
| 2007/0249942 A1 | 10/2007 | Salehi et al. |
| 2007/0287959 A1 | 12/2007 | Walter et al. |
| 2008/0015493 A1 | 1/2008 | Childers et al. |
| 2008/0033342 A1 | 2/2008 | Staggs |
| 2008/0066542 A1 | 3/2008 | Gao |
| 2008/0067046 A1 | 3/2008 | Dacquay et al. |
| 2008/0082040 A1 | 4/2008 | Kubler et al. |
| 2008/0112828 A1 | 5/2008 | Muri et al. |
| 2008/0114289 A1 | 5/2008 | Muri et al. |
| 2008/0114290 A1 | 5/2008 | King et al. |
| 2008/0114291 A1 | 5/2008 | Muri et al. |
| 2008/0114300 A1 | 5/2008 | Muri et al. |
| 2008/0114311 A1 | 5/2008 | Muri et al. |

(56) References Cited

U.S. PATENT DOCUMENTS

| | | | |
|---|---|---|---|
| 2008/0114312 A1 | 5/2008 | Muri et al. |
| 2008/0114372 A1 | 5/2008 | Edwards et al. |
| 2008/0114387 A1 | 5/2008 | Hertweck et al. |
| 2008/0125695 A1 | 5/2008 | Hopkins et al. |
| 2008/0125697 A1 | 5/2008 | Gao |
| 2008/0125698 A1 | 5/2008 | Gerg et al. |
| 2008/0129695 A1 | 6/2008 | Li |
| 2008/0146989 A1 | 6/2008 | Zacharias |
| 2008/0200878 A1 | 8/2008 | Davis et al. |
| 2008/0243105 A1 | 10/2008 | Horvath |
| 2008/0262476 A1 | 10/2008 | Krause et al. |
| 2008/0281253 A1 | 11/2008 | Injev et al. |
| 2008/0294087 A1 | 11/2008 | Steen et al. |
| 2008/0312594 A1 | 12/2008 | Urich et al. |
| 2009/0005712 A1 | 1/2009 | Raney |
| 2009/0005789 A1 | 1/2009 | Charles |
| 2009/0048607 A1 | 2/2009 | Rockley |
| 2009/0087327 A1 | 4/2009 | Voltenburg, Jr. et al. |
| 2009/0124974 A1 | 5/2009 | Crank et al. |
| 2009/0163853 A1 | 6/2009 | Cull et al. |
| 2010/0036256 A1 | 2/2010 | Boukhny et al. |
| 2010/0069825 A1 | 3/2010 | Raney |
| 2010/0069828 A1 | 3/2010 | Steen et al. |
| 2010/0140149 A1 | 6/2010 | Fulkerson et al. |
| 2010/0152685 A1 | 6/2010 | Goh |
| 2010/0185150 A1 | 7/2010 | Zacharias |
| 2010/0249693 A1 | 9/2010 | Links |
| 2010/0280435 A1 | 11/2010 | Raney et al. |
| 2011/0092887 A1 | 4/2011 | Wong et al. |
| 2011/0092924 A1 | 4/2011 | Wong et al. |
| 2011/0092962 A1 | 4/2011 | Ma et al. |
| 2011/0098721 A1 | 4/2011 | Tran et al. |
| 2011/0160646 A1 | 6/2011 | Kadziauskas et al. |
| 2011/0208047 A1 | 8/2011 | Fago |
| 2011/0251569 A1 | 10/2011 | Turner et al. |
| 2011/0300010 A1 | 12/2011 | Jarnagin et al. |
| 2012/0065580 A1 | 3/2012 | Gerg et al. |
| 2012/0078181 A1 | 3/2012 | Smith et al. |
| 2012/0083735 A1 | 4/2012 | Pfouts |
| 2012/0083736 A1 | 4/2012 | Pfouts et al. |
| 2012/0083800 A1 | 4/2012 | Andersohn |
| 2013/0072853 A1 | 3/2013 | Wong et al. |
| 2013/0169412 A1 | 7/2013 | Roth |
| 2013/0184676 A1 | 7/2013 | Kamen et al. |
| 2013/0245543 A1 | 9/2013 | Gerg et al. |
| 2013/0267892 A1 | 10/2013 | Woolford et al. |
| 2013/0289475 A1 | 10/2013 | Muri et al. |
| 2013/0303978 A1 | 11/2013 | Ross |
| 2013/0336814 A1 | 12/2013 | Kamen et al. |
| 2014/0178215 A1 | 6/2014 | Baxter et al. |
| 2014/0188076 A1 | 7/2014 | Kamen et al. |
| 2014/0276424 A1 | 9/2014 | Davis et al. |
| 2016/0151564 A1 | 6/2016 | Magers et al. |

FOREIGN PATENT DOCUMENTS

| | | |
|---|---|---|
| EP | 424687 A1 | 5/1991 |
| EP | 0619993 A1 | 10/1994 |
| EP | 619993 A1 | 10/1994 |
| EP | 1010437 A1 | 6/2000 |
| EP | 1072285 A1 | 1/2001 |
| EP | 1113562 A1 | 7/2001 |
| EP | 1310267 A2 | 5/2003 |
| EP | 1464310 A1 | 10/2004 |
| EP | 1469440 A2 | 10/2004 |
| EP | 1550406 A2 | 7/2005 |
| EP | 1704839 A1 | 9/2006 |
| EP | 1779879 A1 | 5/2007 |
| EP | 1787606 A1 | 5/2007 |
| EP | 1849443 A1 | 10/2007 |
| EP | 1849444 A1 | 10/2007 |
| EP | 1857128 A1 | 11/2007 |
| EP | 1867349 A1 | 12/2007 |
| EP | 1310267 B1 | 1/2008 |
| EP | 1873501 A1 | 1/2008 |
| EP | 1900347 A1 | 3/2008 |
| EP | 1925274 A2 | 5/2008 |
| EP | 1867349 B1 | 11/2008 |
| ES | 2264369 A1 | 12/2006 |
| GB | 2230301 A | 10/1990 |
| GB | 2352887 A | 2/2001 |
| GB | 2438679 A | 12/2007 |
| JP | S5724482 A | 2/1982 |
| JP | S58167333 A | 10/1983 |
| JP | S62204463 A | 9/1987 |
| JP | 2005195653 A | 7/2005 |
| JP | 2008188110 A | 8/2008 |
| WO | 9220310 A1 | 11/1992 |
| WO | 9315777 A2 | 8/1993 |
| WO | 9317729 A1 | 9/1993 |
| WO | 9324082 A1 | 12/1993 |
| WO | 9405346 A1 | 3/1994 |
| WO | 9632144 A1 | 10/1996 |
| WO | 9737700 A1 | 10/1997 |
| WO | 9818507 A1 | 5/1998 |
| WO | 9917818 A1 | 4/1999 |
| WO | 0000096 A1 | 1/2000 |
| WO | 0070225 A1 | 11/2000 |
| WO | 0122696 A1 | 3/2001 |
| WO | 0226286 A2 | 4/2002 |
| WO | 0228449 A2 | 4/2002 |
| WO | 0234314 A1 | 5/2002 |
| WO | 03102878 A1 | 12/2003 |
| WO | 04096360 A1 | 11/2004 |
| WO | 2004114180 A1 | 12/2004 |
| WO | 05084728 A2 | 9/2005 |
| WO | 05092023 A2 | 10/2005 |
| WO | 05092047 A2 | 10/2005 |
| WO | 06101908 A2 | 9/2006 |
| WO | 06125280 A1 | 11/2006 |
| WO | 2007121144 A1 | 10/2007 |
| WO | 2007143677 A2 | 12/2007 |
| WO | 2007143797 A1 | 12/2007 |
| WO | 2007149637 A2 | 12/2007 |
| WO | 2008030872 A1 | 3/2008 |
| WO | 2008060859 A1 | 5/2008 |
| WO | 2008060902 A1 | 5/2008 |
| WO | 2008060995 A1 | 5/2008 |
| WO | 2009123547 A1 | 10/2009 |
| WO | 2010054146 A1 | 5/2010 |
| WO | 2010054225 A2 | 5/2010 |
| WO | 2010151704 A1 | 12/2010 |
| WO | 2012151062 A1 | 11/2012 |
| WO | 2013142009 A1 | 9/2013 |
| WO | 2015009945 A1 | 1/2015 |

OTHER PUBLICATIONS

English Human Translation of JP57024482 from Feb. 9, 1982.
European Search Report for Application No. EP16199518, dated Mar. 22, 2017, 9 pages.
European Search Report for Application No. EP16202917, dated May 2, 2017, 6 pages.
Boyd, "Preparing for the Transition" in: The Art and the Science of Cataract Surgery, Chapter 7, 2001, pp. 93-133.
Definition of "Parameter", Retrieved from the Internet:, Retrieved on Aug. 9, 2016.
European Search Report for Application No. EP10164058, dated Jun. 25, 2010, 2 pages.
European Search Report for Application No. EP13184138.9, dated Oct. 24, 2013, 7 pages.
Examination Report dated Mar. 28, 2012 for European Application No. EP09791072 filed Jul. 31, 2009, 3 pages.
International Search Report and Written Opinion for Application No. PCT/US2015/066036, dated Jul. 4, 2016, 20 pages.
International Search Report and Written Opinion for Application No. PCT/US2016/049970, dated Dec. 5, 2016, 12 pages.
International Search Report and Written Opinion for Application No. PCT/US2016/061648, dated Feb. 7, 2017, 12 pages.
Merritt R., et al., Wireless Nets Starting to link Medical Gear [online] 2004 [retrieved on Feb. 12, 2007]. Retrieved from the Internet: 3 pages.

(56) References Cited

OTHER PUBLICATIONS

Phacoemulsification, [online] [retrieved on Jul. 1, 2009]. Retrieved from the Internet:, 2 pages.

* cited by examiner

AUTOMATICALLY SWITCHING DIFFERENT ASPIRATION LEVELS AND/OR PUMPS TO AN OCULAR PROBE

This application is a divisional of and claims priority to U.S. application Ser. No. 12/614,093, filed on Nov. 6, 2009, which claims priority to U.S. Application No. 61/198,626 filed on Nov. 7, 2008, the entirety of which are hereby incorporated by reference.

FIELD OF THE INVENTION

The present invention relates generally to the field of surgery, and more specifically to devices, systems, and methods for treatment of an eye. Exemplary embodiments allow enhanced treatment to structures within an eye by at least once (though more commonly repeatedly or even cyclically) applying different levels and/or types of aspiration to an ocular probe, often such that the aspiration changes during a treatment of a particular eye.

BACKGROUND OF THE INVENTION

The present invention is generally related to methods, devices, and systems for controlling surgical fluid flows, particularly during treatment of an eye. In exemplary embodiments, the invention removes material from within the eye in part by a displacement-induced aspiration flow (such as that caused by a peristaltic or other positive displacement pump), and in part by a vacuum-induced aspiration flow (such as that caused by a venturi pump). Optionally, the aspiration flow may switch between a displacement pump and a venturi pump while material is being fragmented and removed from within the eye. While the system operator will typically have control over the overall mode of operation throughout a procedure, switching between these two different types of aspiration flow may occur "on-the-fly" without halting of a corresponding irrigation flow, and without awaiting input from the system operator regarding that particular flow change. The material may be removed from an anterior or posterior chamber of the eye, such as for phacoemulsification of cataracts, treatment of retinal diseases, vitrectomy, and the like.

The optical elements of the eye include both a cornea (at the front of the eye) and a lens within the eye. The lens and cornea work together to focus light onto the retina at the back of the eye. The lens also changes in shape, adjusting the focus of the eye to vary between viewing near objects and far objects. The lens is found just behind the pupil, and within a capsular bag. This capsular bag is a thin, relatively delicate structure which separates the eye into anterior and posterior chambers.

With age, clouding of the lens or cataracts is fairly common. Cataracts may form in the hard central nucleus of the lens, in the softer peripheral cortical portion of the lens, or at the back of the lens near the capsular bag.

Cataracts can be treated by the replacement of the cloudy lens with an artificial lens. Phacoemulsification systems often use ultrasound energy to fragment the lens and aspirate the lens material from within the capsular bag. This may allow the remaining capsular bag to be used for positioning of the artificial lens, and maintains the separation between the anterior portion of the eye and the vitreous humour in the posterior chamber of the eye.

During cataract surgery and other therapies of the eye, accurate control over the volume of fluid within the eye is highly beneficial. For example, while ultrasound energy breaks up the lens and allows it to be drawn into a treatment probe with an aspiration flow, a corresponding irrigation flow may be introduced into the eye so that the total volume of fluid in the eye does not change excessively. If the total volume of fluid in the eye is allowed to get too low at any time during the procedure, the eye may collapse and cause significant tissue damage. Similarly, excessive pressure within the eye may strain and injure tissues of the eye.

While a variety of specific fluid transport mechanisms have been used in phacoemulsification and other treatment systems for the eyes, aspiration flow systems can generally be classified in two categories: 1) volumetric-based aspiration flow systems using positive displacement pumps; and 2) vacuum-based aspiration systems using a vacuum source, typically applied to the aspiration flow through an air-liquid interface. Among positive displacement aspiration systems, peristaltic pumps (which use rotating rollers that press against a flexible tubing to induce flow) are commonly employed. Such pumps provide accurate control over the flow volume. The pressure of the flow, however, is less accurately controlled and the variations in vacuum may result in the feel or traction of the handpiece varying during a procedure. Peristaltic and other displacement pump systems may also be somewhat slow for some procedures. Vacuum rise times tend to be slower for peristaltic systems than venturi systems. This may result in an overall sluggish feel to the surgeon. Moreover, the ultrasonic vibrations of a phacoemulsification tip may (despite peristaltic aspiration flow into the tip) inhibit the desired fragmentation-inducing engagement between the tip and tissue particles.

Vacuum-based aspiration systems provide accurate control over the fluid pressure within the eye, particularly when combined with gravity-fed irrigation systems. While vacuum-based systems can (in some circumstances) result in excessive fluid flows, they may have advantages when, for example, it is desired to bring tissue fragments to the probe, or when removing a relatively large quantity of the viscous vitreous humour from the posterior chamber of the eye. Unfortunately, venturi pump and other vacuum-based aspiration flow systems are subject to pressure surges during occlusion of the treatment probe, and such pressure surges may decrease the surgeon's control over the eye treatment procedure. Displacement pump systems are similarly subject to vacuum spikes during and immediately following occlusion of the probe.

While there have been prior proposals for multiple pump systems which make use of either a positive displacement pump or a vacuum source, the previously proposed systems have not been ideal. Hence, to provide surgeons with the benefits of both vacuum-based and displacement-based aspiration flows, still further improvements appear desirable. In particular, interrupting a procedure to switch between aspiration systems may be inconvenient, and it may be difficult or even impossible to take full advantage (for example) of the full potential of combining both vacuum-based and displacement-based aspiration flows using prior eye treatment systems.

In light of the above, it would be advantageous to provide improved devices, systems, and methods for eye surgery. It would be particularly advantageous if these improvements allowed system users to maintain the benefits of vacuum and/or displacement fluid control systems when appropriate, and without having to interrupt the procedure to manually switch pumps, change handpieces or other system components, or the like. Ideally, these improved systems would provide benefits beyond those of peristaltic or venturi systems alone, such as combination peristaltic/venturi systems, without delaying the procedure or increasing the complexity of the operation to the system operator.

BRIEF SUMMARY OF THE INVENTION

One embodiment of the invention may include a method for applying aspiration to a probe. The method may be computer implemented. The method may include applying a base vacuum level from a first pump to a probe to achieve a base level flow-rate, applying a secondary vacuum level from a second pump to the probe to achieve an additive level flow-rate, which is additional to the base level flow-rate, and detecting that the probe is at least partially occluded by detecting an increased secondary vacuum level.

Another embodiment of the invention may include a method for removing material from an eye. The method may include generating a base level aspiration flow by applying a base aspiration pressure differential using a pressure pump to an aspiration flow pathway from the eye, generating an additive level flow, during the base level flow, by pumping the additive level flow with a volumetric pump, and detecting occlusion of the aspiration flow pathway by detecting an increased pressure differential above the base pressure differential generated by the volumetric pump.

Yet another embodiment of the invention may include a system for removing material from within an eye. The system may include a probe having a distal tip insertable into the eye, wherein the tip comprises an aspiration port, and a console coupled with/to the port along an aspiration pathway, wherein the console comprises a processor and a pump system for providing a base level aspiration flow by applying a base aspiration pressure differential and an additive level flow, during the base level flow, wherein the processor is configured to detect occlusion of the aspiration flow pathway by detecting an increased pressure differential above the base pressure. The pump system may comprise multiple pumps, including a first pump and a second pump, wherein the first pump and the second pump may be a vacuum based (pressure) pump and/or a flow based (volumetric) pump.

Yet another embodiment of the invention may include a method for applying aspiration and irrigation to a phacoemulsification device. The method may be computer implemented. The method may include applying a low flow-rate aspiration from a first pump to an aspiration port of a probe, applying a low flow-rate irrigation from a fluid source to an irrigation port of the probe while applying the low flow-rate aspiration, transitioning from the low flow rate aspiration to a high flow-rate aspiration from a second pump to the aspiration port, and transitioning from the low flow-rate irrigation to a high flow-rate irrigation while transitioning from the low flow-rate aspiration to the high flow-rate aspiration.

Yet another embodiment of the invention may include a system for removing material from within an eye. The system may include a probe having a distal tip insertable into the eye, wherein the tip comprises an aspiration port and an irrigation port, and a console coupled with/to the port along an aspiration pathway, wherein the console comprises a processor and a pump system for providing a first pump rate and a second pump rate higher than the first pump rate, and a irrigation system for providing a variable irrigation rate, the processor configured to automatically switch from the first pump rate to the second pump rate and vary the irrigation rate according to the pump rates. The pump system may comprise multiple pumps, including a first pump and second pump.

Yet another embodiment of the invention may include a method for applying aspiration to a probe. The method may be computer implemented. The method may include applying a aspiration flow-rate first pump to a probe to achieve a first level flow-rate, tracking a vacuum level to control aspiration of probe, setting a threshold vacuum level, switching from the first level flow-rate to a second level flow-rate from a second pump, and tracking flow rate to control the aspiration of the probe when the threshold vacuum level is passed. The method may include switching from the first pump to a second pump, while maintaining the same flow-rate.

Yet another embodiment of the invention may include a system for removing material from within an eye. The system may include a probe having a distal tip insertable into the eye, wherein the tip comprises an aspiration port, and a console coupled with/to the port along an aspiration pathway, wherein the console comprises a processor and a pump system for providing a first pump rate and a second pump rate higher than the first pump rate. Further, the processor is configured to automatically switch from the first pump rate to the second pump rate and control aspiration of the probe by tracking a vacuum level up to a threshold, and control aspiration of the probe by tracking a flow rate of the probe when the threshold has been passed. The pump system may comprise multiple pumps, including a first pump and a second pump.

Yet another embodiment of the invention may a include a phacoemulsification system, comprising a handpiece, wherein the handpiece comprises a needle having at least one port and wherein the needle is configured to move in a substantially longitudinal and a non-longitudinal direction; a first pump, wherein the first pump is configured to operate when a longitudinal cutting mode is selected; and a second pump, wherein the second pump is configured to operate when a non-longitudinal cutting mode is selected. The first pump may comprise a flow based pump and the second pump may comprise a vacuum based pump. Alternatively, the first pump may comprise a vacuum based pump and the second pump may comprise a vacuum based pump. Further, the non-longitudinal direction may be selected from the group consisting of transversal and torsional. The invention may further comprise a foot pedal, wherein the foot pedal is configured to move in a first direction and a second direction, wherein the first direction is configured to control the first pump and the second direction is configured to control the second pump. The first direction and the second direction may be selected from the group consisting of yaw and pitch.

To better understand the nature and advantages of the invention, reference should be made to the following description and the accompanying figures. It is to be understood, however, that each of the figures is provided for the purpose of illustration only and is not intended as a definition of the limits of the scope of the present invention.

DETAILED DESCRIPTION OF THE INVENTION

Figure 1:
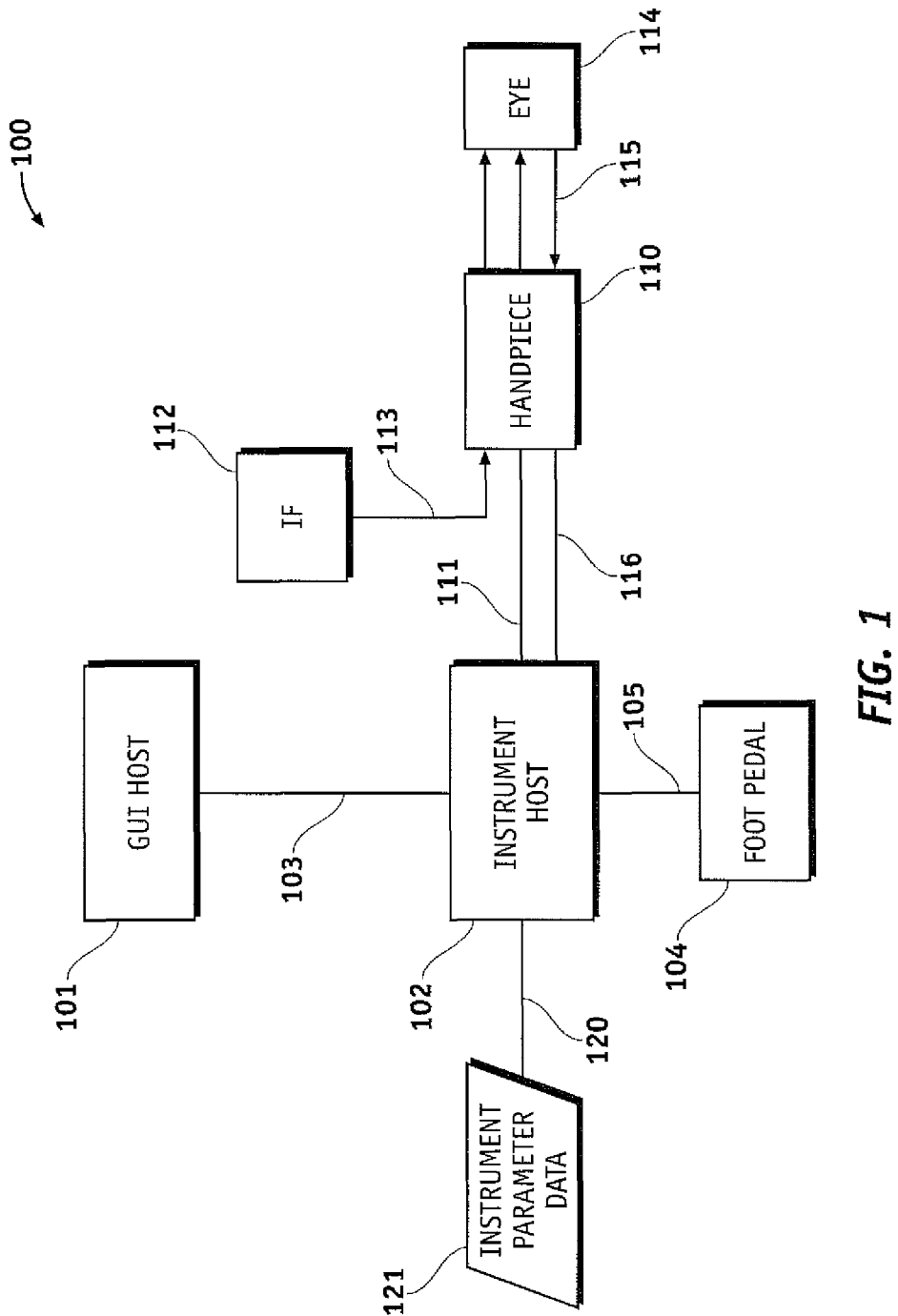
FIG. 1 illustrates an exemplary phacoemulsification/vitrectomy irrigation/aspiration system in a functional block diagram to show the components and interfaces for a safety critical medical instrument system that may be employed in accordance with an embodiment of the present invention.

FIG. 1 illustrates an exemplary phacoemulsification/vitrectomy system 100 in a functional block diagram to show the components and interfaces for a safety critical medical instrument system that may be employed in accordance with an aspect of the present invention. A serial communication cable 103 connects GUI host 101 module and instrument host 102 module for the purposes of controlling the surgical instrument host 102 by the GUI host 101. GUI host 101 and instrument host 102, as well as any other component of system 100, may be connected wirelessly. Instrument host 102 may be considered a computational device in the arrangement shown, but other arrangements are possible. An interface communications cable 120 is connected to instrument host 102 module for distributing instrument sensor data 121, and may include distribution of instrument settings and parameters information, to other systems, subsystems and modules within and external to instrument host 102 module. Although shown connected to the instrument host 102 module, interface communications cable 120 may be connected or realized on any other subsystem (not shown) that could accommodate such an interface device able to distribute the respective data.

A switch module associated with foot pedal 104 may transmit control signals relating internal physical and virtual switch position information as input to the instrument host 102 over serial communications cable 105 (although foot pedal 104 may be connected wireless, e.g. Bluetooth, IR). Instrument host 102 may provide a database file system for storing configuration parameter values, programs, and other data saved in a storage device (not shown). In addition, the database file system may be realized on the GUI host 101 or any other subsystem (not shown) that could accommodate such a file system. The foot pedal system (104) can be configured as dual linear. In this configuration, the surgeon can dictate the system to operate with the peristaltic pump in the traditional pitch and add the venturi vacuum with the yaw mechanism. This will allow a surgeon the control of peristaltic operation with the added efficiency of venturi operation. The foot pedal 104 can also combine longitudinal cutting modes with a certain pump and non-longitudinal cutting modes (i.e., transversal, torsion, etc.) with a different pump for example, the foot pedal pitch could control a peristaltic pump with longitudinal ultrasonic cutting, and the yaw could control the venturi pump with non-longitudinal cutting. The foot pedal can also be configured to operate using a certain pump by yawing to the left and operate a second pump by yawing to the right. This gives the user the ability to switch-on-the-fly without accessing the user interface which may be timely and cumbersome. Control of one or more pumps may be programmed to the pitch and/or yaw directional movement of a treadle of foot pedal 104 and/or to any switch located on foot pedal 104

The phacoemulsification/vitrectomy system 100 has a handpiece 110 that includes a needle and electrical means, typically a piezoelectric crystal, for ultrasonically vibrating the needle. The instrument host 102 supplies power on line 111 to a phacoemulsification/vitrectomy handpiece 110. An irrigation fluid source 112 can be fluidly coupled with/to handpiece 110 through line 113. The irrigation fluid and ultrasonic power are applied by handpiece 110 to an eye, or affected area or region, indicated diagrammatically by block 114. Alternatively, the irrigation source may be routed to eye 114 through a separate pathway independent of the handpiece. Aspiration is provided to eye 114 by one or more pumps (not shown), such as a peristaltic pump, via the instrument host 102, through lines 115 and 116. A surgeon/operator may select an amplitude of electrical pulses either using the handpiece, foot pedal, via the instrument host and/or GUI host, and/or by voice command.

The instrument host 102 generally comprises at least one processor board. Instrument host 102 may include many of the components of a personal computer, such as a data bus, a memory, input and/or output devices (including a touch screen (not shown)), and the like. Instrument host 102 will often include both hardware and software, with the software typically comprising machine readable code or programming instructions for implementing one, some, or all of the methods described herein. The code may be embodied by a tangible media such as a memory, a magnetic recording media, an optical recording media, or the like. A controller (not shown) may have (or be coupled with/to) a recording media reader, or the code may be transmitted to instrument host 102 by a network connection such as an internet, an intranet, an Ethernet, a wireless network, or the like. Along with programming code, instrument host 102 may include stored data for implementing the methods described herein, and may generate and/or store data that records parameters reflecting the treatment of one or more patients.

In combination with phacoemulsification system 100, the present system enables aspiration, venting, or reflux functionality in or with the phacoemulsification system and may comprise components including, but not limited to, a flow selector valve, two or more pumps, a reservoir, and a collector, such as a collection bag or a device having similar functionality. The collector in the present design collects aspirant from the ocular surgical procedure.

Figure 2A:
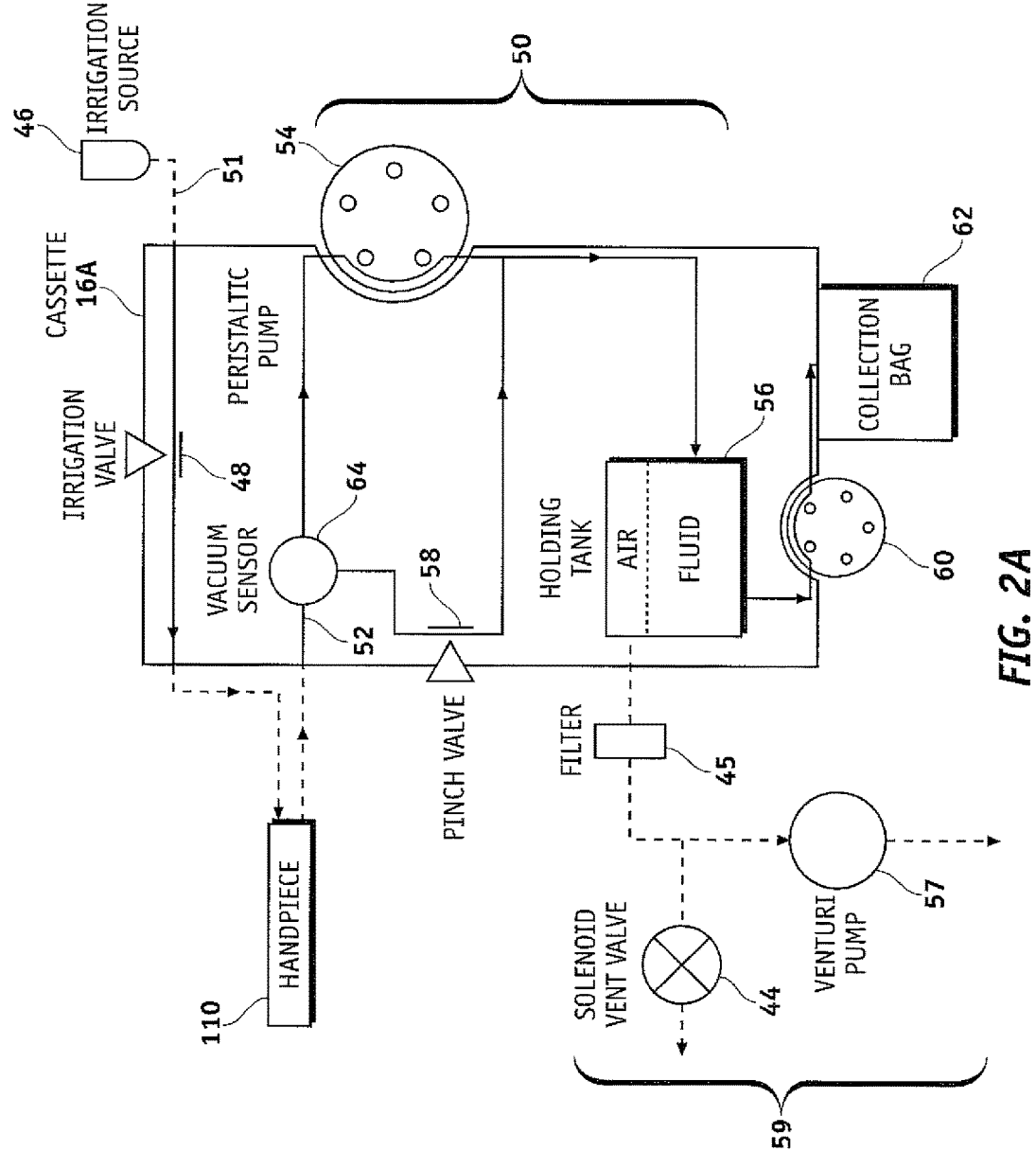
FIGS. 2A and 2B are a functional block diagrams of an exemplary surgical cassette venting systems, according to embodiments of the invention.

FIG. 2A illustrates an exemplary surgical cassette system in a functional block diagram that shows the components and interfaces that may be employed in accordance with an aspect of the present design. An irrigation source 46 of, and/or controlled by, instrument host 102 optionally provides irrigation fluid pressure control via an irrigation line 51 by relying at least in part on a gravity pressure head that varies with a height of an irrigation fluid bag or the like. An irrigation on/off pinch valve 48 may generally include a short segment of a flexible conduit of cassette 16A, which can be engaged and actuated by an actuator of the instrument host 102, with a surface of the cassette body often being disposed opposite the actuator to facilitate closure of the conduit lumen. Alternative irrigation flow systems may include positive displacement pumps, alternative fluid pressurization drive systems, fluid pressure or flow modulating valves, and/or the like.

In certain embodiments, irrigation fluid is alternatively or additionally provided to a separate handpiece (not shown). The aspiration flow network 50 generally provides an aspiration flow path 52 that can couple an aspiration port in the tip of handpiece 110 to either a peristaltic pump 54, formed by engagement of cassette 16A with instrument host 102, and/or a holding tank 56. Fluid aspirated through the handpiece 110 may be contained in holding tank 56 regardless of whether the aspiration flow is induced by peristaltic pump 54 or the vacuum applied to the holding tank 56 via pump 57. When pinch valve 58 is closed and peristaltic pump 54 is in operation, pumping of the aspiration flow may generally be directed by the peristaltic pump 54, independent of the pressure in the holding tank 56. Conversely, when peristaltic pump 54 is off, flow through the peristaltic pump may be halted by pinching of the elastomeric tubing arc of the peristaltic pump by one or more of the individual rollers of the peristaltic pump rotor. Hence, any aspiration fluid drawn into the aspiration network when peristaltic pump 54 is off will typically be effected by opening of a pinch valve 58 so that the aspiration port of the probe is in fluid communication with the holding tank. Regardless, the pressure within tank 56 may be maintained at a controlled vacuum level, often at a fixed vacuum level, by a vacuum system 59 of instrument host 102.

Vacuum system 59 may comprise a Venturi pump 57, a rotary vane pump, a vacuum source, a vent valve 44, a filter and/or the like. Aspiration flow fluid that drains into holding tank 56 may be removed by a peristaltic drain pump 60 and directed to a disposal fluid collection bag 62. Vacuum pressure at the surgical handpiece 110 may be maintained within a desired range through control of the fluid level in the holding tank. In particular, peristaltic drain pump 60 enables the holding tank 56 to be drained including, while vacuum-based aspiration continues using vacuum system 59. In more detail, the operation of aspiration flow network 50 can be understood by first considering the flow when pinch valve 58 is closed. In this mode, peristaltic pump 54 draws fluid directly from handpiece 110, with a positive displacement peristaltic pump flow rate being controlled by a system controller. To determine the appropriate flow rate, the level of vacuum within the aspiration flow network may be identified in part with reference to a vacuum sensor 64 with three ports disposed along the aspiration flow network 50 between peristaltic pump 54, handpiece 110, and pinch valve 58. This allows the system to detect and adjust for temporary occlusions of the handpiece 110 and the like. Venting or reflux of the handpiece 110 in this state may be achieved by reversing the rotation of peristaltic pump 54 or by opening pinch valve 58 to equalize fluid pressures. Pinch valve 58 may be configured as a variable restrictor to regulate the amount of fluid that is vented and/or refluxed from the high pressure side of peristaltic pump 54 to the low pressure side. In this mode, while the aspiration material flows through holding tank 56 and eventually into collection bag 62, the holding tank pressure may have little or no effect on the flow rate. When peristaltic pump 54 is not in operation, rotation of the peristaltic pump may be inhibited and the rotors of the peristaltic pump generally pinch the arcuate resilient tubing of the probe so as to block aspiration flow. Material may then be drawn into the aspiration port of handpiece 110 by opening pinch valve 58 and engagement or operation of the vacuum system 59. When valve 58 is open, the aspiration port draws fluid therein based on the pressure differential between holding tank 56 and the chamber of the eye in which the fluid port is disposed, with the pressure differential being reduced by the total pressure loss of the aspiration flow along the aspiration path between the tank and port. In this mode, venting or reflux of the handpiece 110 may be accomplished by opening the solenoid vent valve 44, which pressurizes the holding tank 56 to increase the tank pressure and push fluid back towards (i.e., "vents") the tubing and/or handpiece 110.

In some embodiments, the vent valve 44 may be used to increase the pressure inside the tank 56 to at or near atmospheric pressure. Alternatively, venting of the handpiece 110 may be accomplished in this mode by closing pinch valve 58, and by rotation peristaltic pump 54 in reverse (e.g., clockwise in FIG. 2A). Accordingly, aspiration network 50 allows system 100 to operate in either flow-based (e.g. peristaltic) and/or vacuum-based (e.g. Venturi) pumping modes and to incorporate three different venting modes. In some embodiments, an additional valve is added that may be used to fluidly couple the irrigation line 51 to the aspiration flow network 50, thus providing an addition option for venting or refluxing the handpiece 110.

Figure 2B:
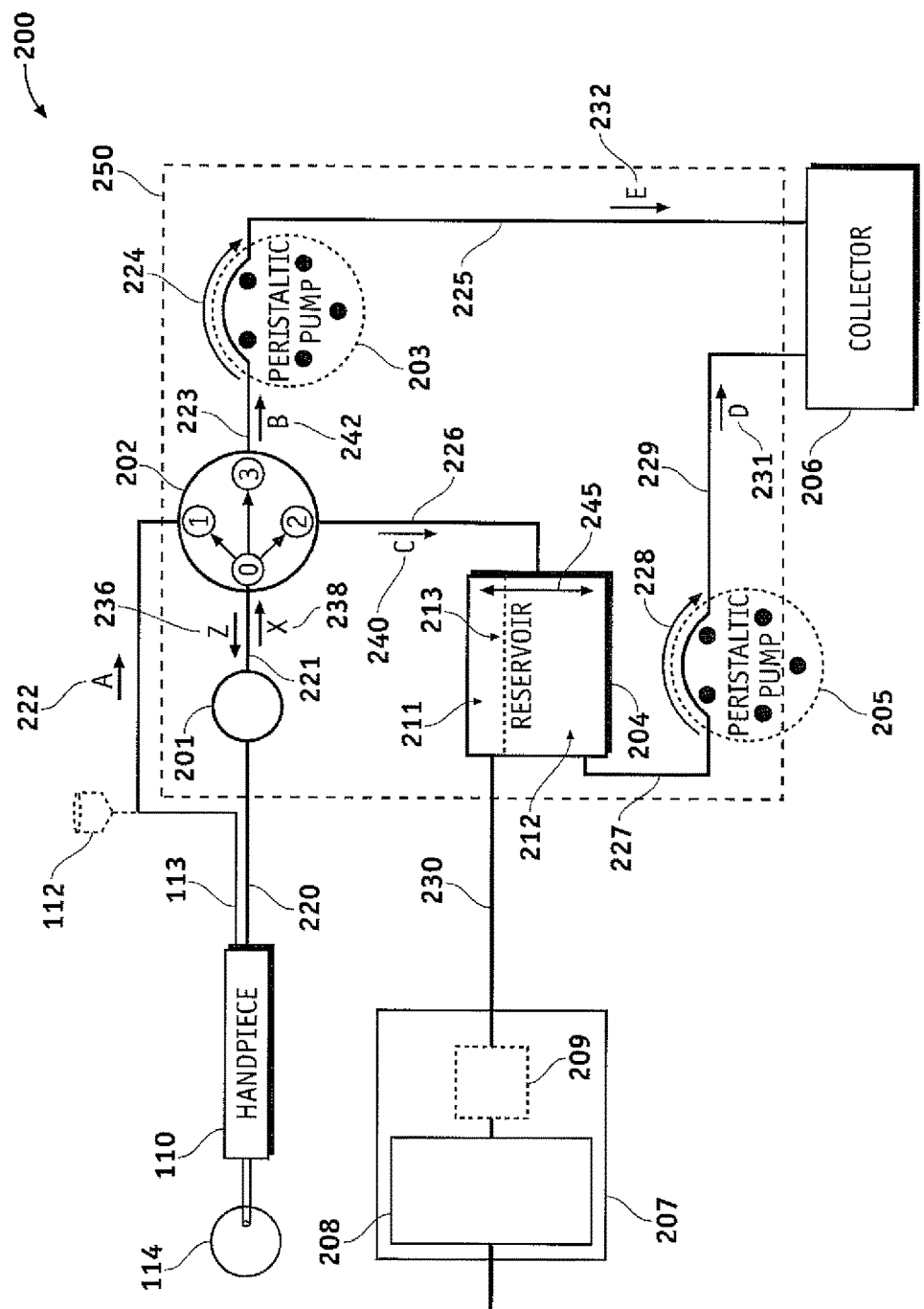

FIG. 2B illustrates another exemplary surgical cassette system in a functional block diagram that shows the components and interfaces that may be employed in accordance with an aspect of the present design.

The present design effectively splits the aspiration line from handpiece 110 into at least two separate fluid pathways where one is connected to collector 206 and the other to the air/fluid reservoir 204, which is also connected to collector 206. Splitting the fluid pathways in this way allows one line designated for vacuum regulated aspiration, venting, and/or reflux and the other line designated for peristaltic aspiration, venting, and/or reflux. However, the aspiration line, or the at least two separate fluid pathways may be connected with air/fluid reservoir 204. The vacuum regulated aspiration line 226 connects to reservoir 204, wherein fluid may be aspirated, vented, and/or refluxed to or from reservoir 204 through the line 226. The peristaltic line connects directly to the collector and aspirates, vents, and/or refluxes through the aspiration line 223, 225 without requiring a connection to reservoir 204.

Surgical cassette venting system 200 may include a fluid vacuum sensor 201, flow selector valve 202, reservoir 204, collector 206, and fluid pathways, such as interconnecting surgical tubing, as shown in FIG. 2B. The cassette arrangement 250 may include connections to facilitate easy attachment to and removal from the instrument host 102 as well as handpiece 110 and vacuum pump arrangement 207. The present design contemplates two or more pumps, where the surgical cassette arrangement may operate with fluid pathways or other appropriate fluid interconnections interfacing with the two or more pumps.

Cassette arrangement 250 is illustrated in FIG. 2B to simply show components that may be enclosed within the cassette. The size and shape of cassette 250 is not to scale nor accurately sized, and note that certain components, notably peristaltic pump 203, interface with the cassette but in actuality form part of the device which the cassette attaches to. Further, more or fewer components may be included in the cassette than are shown in FIGS. 2A and 2B depending on the circumstances and implementation of the cassette arrangement 250.

Referring to FIG. 2B, handpiece 110 is connected to the input side of fluid vacuum sensor 201, typically by fluid pathways such as fluid pathway 220. The output side of fluid vacuum sensor 201 is connected to flow selector valve 202 within cassette arrangement 250 via fluid pathway 221. The present design may configure flow selector valve 202 to interface between handpiece 110, balanced saline solution (BSS) fluid bottle 112, pump 203, which is shown as a peristaltic pump but may be another type of pump, and reservoir 204. In this configuration, the system may operate flow selector valve 202 to connect handpiece 110 with BSS fluid bottle 112, reservoir 204 or with pump 203 based on signals received from instrument host 102 resulting from the surgeon's input to GUI host 101.

The flow selector valve 202 illustrated in FIG. 2B provides a single input port and may connect port '0' to one of three available ports numbered '1', '2', and '3'. The present design is not limited to one flow selector valve, and may be realized using two flow selector valves each having at least two output ports, possibly connected together to provide the functionality described herein. For example, a pair of two output port valves may be configured in a daisy chain arrangement, where the output port of a first valve is directly connected to the input port of a second valve. The instrument host may operate both valves together to provide three different flow configurations. For example, using two valves, valve one and valve two, valve one may use output port one, which is the supply for valve two. Valve two may connect to one of two ports providing two separate paths. When valve one connects its input port to its second output port rather than the output port that directs flow to the second valve, a third path is provided.

Thus while a single flow selector valve 202 is illustrated in FIG. 2B, it is to be understood that this illustration represents a flow selector valve arrangement, including one or more flow selector valves performing the functionality described herein, and is not limited to a single device or a single flow selector valve. It is also contemplated that flow selector valve 202 may be a pinch valve or multiple pinch valves as shown in FIG. 2A, and for example as shown in co-assigned U.S. patent application Ser. No. 11/937,456, the entirety of which is incorporated by reference herein. It is also contemplated that flow selector valve 202 and fluid vacuum sensor 201 may be a single unit, e.g. fluid vacuum sensor 201 may comprise or be a part of flow selector valve 202.

It is also envisioned that flow selector valve 202 may be or comprise one or more pinch valves. The one or more pinch valves may be located along fluid pathway 221 and/or 223, or any other fluid pathway as discussed herein. Further, there may be one or more fluid pathways couples with handpiece 110 and extending to various components of cassette arrangement 250, including a first fluid pathway from fluid vacuum sensor 201 to collector 206 via pump 203 and/or a second fluid pathway to reservoir 204. In another embodiment, fluid pathway 220 is a single fluid pathway that couples with fluid vacuum sensor 201. From fluid vacuum sensor 201, the single fluid pathway 220 may divide into two fluid pathways, one to collector 206 via pump 203 and one to reservoir 204. Further, one or more pinch valves and/or flow selector valve 202 may be located along the fluid pathway between fluid vacuum sensor 201 and collector 206 and/or between fluid vacuum sensor 201 and reservoir 204.

The present design's fluid vacuum sensor 201, for example a strain gauge or other suitable component, may communicate or signal information to instrument host 102 to provide the amount of vacuum sensed in the handpiece fluid pathway 220. Instrument host 102 may determine the actual amount of vacuum present based on the communicated information.

Fluid vacuum sensor 201 monitors vacuum in the line, and can be used to determine when flow should be reversed, such as encountering a certain pressure level (e.g. in the presence of an occlusion), and based on values obtained from the fluid vacuum sensor 201, the system may control selector valve 202 and the pumps illustrated or open the line to reflux from irrigation. It is to be understood that while components presented in FIG. 2B and other drawings of the present application are not shown connected to other system components, such as instrument host 102, but are in fact connected for the purpose of monitoring and control of the components illustrated. Flow selector valve 202 and fluid vacuum sensor 201 may also exist as a single unit.

With respect to fluid vacuum sensor 201, emergency conditions such as a dramatic drop or rise in pressure may result in a type of fail-safe operation. The present design employs fluid vacuum sensor 201 to monitor the vacuum conditions and provide signals representing vacuum conditions to the system such as via instrument host 102 for the purpose of controlling components shown including, but not limited to flow selector valve 202 and the pumps shown. Alternative embodiments may include flow sensors (not shown).

Multiple aspiration and ventilation options are available in the design of FIG. 2B. In the arrangement where the selector valve 202 connects handpiece 110 with BSS bottle 112, the present design allows for venting of fluid from BSS bottle 112 to eye 114 as indicated by directional flow arrow 'Z' 236 and arrow 'A' 222 in FIG. 2B. In the arrangement where the flow selector valve 202 connects handpiece 110 with peristaltic pump 203, the present design may allow for aspiration from eye 114 directly to collector 206 as indicated by flow indicated in the directions of 'X' 238, arrow B 242, and arrow E at 232 as illustrated in FIG. 2B. Reversing direction of pump 203 can result in venting and/or refluxing.

In the arrangement where the cassette system flow selector valve 202 connects handpiece 110 with reservoir 204, the present design allows for aspiration from eye 114 directly to reservoir 204 as indicated by directional flow arrow 'X' 238, and arrow C 240 in FIG. 2B. Arrows/directions 238, 242, and 232 illustrate the flow of fluid for peristaltic pumping. Arrow 224 indicates the direction of operation for peristaltic pump 203 where fluid originating at handpiece 110 is pumped through line 223 toward line 225 during aspiration. Arrows/directions 238 and 240 illustrate the flow of fluid for venturi pumping.

Although venting is shown from BSS bottle 112, venting and/or irrigation is not represented in FIG. 2B via the pumps. However, the present design may allow for venting and/or reflux using the pumps associated with the cassette where the arrows in FIG. 2B are reversed; for example, indicating pump 203 is reversed or operates in a counter-clockwise direction. In this arrangement, the design may effectively split the aspiration line from the handpiece into two distinct lines, one arranged for peristaltic operation and the second line arranged for vacuum regulated operation via an air/fluid reservoir.

Reservoir 204 may contain air in section 211 and fluid in section 212. Surgical cassette system 200 may connect reservoir 204 with collector 206 using fluid pathways, such as surgical tubing or similar items. In this arrangement, pump 205 may operate in a clockwise direction in the direction of arrow 228 to remove fluid from the reservoir 204 through fluid pathway 227 and deliver the fluid to collector 206 using fluid pathway 229. The present design illustrates a peristaltic pump as pump 205, a component within instrument host 102, but other types of pumps may be employed. This configuration may enable the surgical cassette 200 to remove unwanted fluid and/or material from reservoir 204.

The fluid pathways or flow segments of surgical cassette system 200 may include the fluid connections, for example flexible tubing, between each component represented with solid lines in FIG. 2B.

Vacuum pump arrangement 207 is typically a component within instrument host 102, and may be connected with reservoir 204 via fluid pathway or flow segment 230. In the configuration shown, vacuum pump arrangement 207 includes a pump 208, such as a venturi pump and an optional pressure regulator 209 (and valve (not shown)), but other configurations are possible. In this arrangement, vacuum pump arrangement 207 may operate to remove air from the top of reservoir 204 and deliver the air to atmosphere (not shown). Removal of air from reservoir 204 in this manner may reduce the pressure within the reservoir, which reduces the pressure in the attached fluid pathway 226, to a level less than the pressure within eye 114. A lower reservoir pressure connected through flow selector valve 202 may cause fluid to move from the eye, thereby providing aspiration. The vacuum pump arrangement 207 and reservoir 204 can be used to control fluid flow into and out of reservoir 204. Vacuum pump arrangement 207 may also be used to vent the aspiration line to air by opening a valve to the venturi pump.

The optional pressure regulator 209 may operate to add air to the top of reservoir 204 which in turn increases pressure and may force the air-fluid boundary 213 to move downward. Adding air into reservoir 204 in this manner may increase the air pressure within the reservoir, which increases the pressure in the attached fluid aspiration line 226 to a level greater than the pressure within eye 114. A higher reservoir pressure connected through flow selector valve 203 may cause fluid to move toward eye 114, thereby providing venting or reflux.

An alternate method of creating positive pressure in reservoir 204 is running pump 205 in a counter-clockwise direction. Running pump 205 in a counter-clockwise direction will increase the amount of air in section 211 in reservoir 204.

It is to be noted that higher pressure in reservoir 204 causes more fluid flow and potentially more reflux from reservoir 204 to handpiece 110. If the lines from the reservoir 204 are plugged or otherwise occluded, providing pressure to reservoir 204 can result in venting and/or reflux. Venting in this context results in the release of pressure. Reflux occurs when a pump is reversed sending fluid in the opposite direction of normal flow (e.g. toward the eye). In a reflux condition, the surgeon can control the amount of fluid flowing back through the fluid pathways and components.

The present design may involve peristaltic operation, aspirating fluid from eye 114 to collector 206 illustrated in FIG. 2B, or venting fluid to the eye 114 to reduce the amount of pressure in the aspiration line (where such venting is only shown from BSS bottle 112 in FIG. 2). Peristaltic pumping is generally understood to those skilled in the art, and many current machines employ peristaltic and/or venturi pumps as the vacuum or pressure sources. Generally, a peristaltic pump has fluid flowing through a flexible tube and a circular rotor with a number of rollers attached to the periphery of the circular rotor. As the rotor turns, fluid is forced through the tube. Venturi pumping, or pressure or aspiration or aspirator pumping, produces the vacuum using the venturi effect by providing fluid through a narrowing tube. Because of the narrowing of the tube, the speed at which the fluid travels through the tube increases and the fluid pressure decreases (the "Venturi effect"). As may be appreciated, operating pumps in one direction or another can change the pressure and the operation of the associated device, such as the operation of the cassette in the present design.

Figure 3:
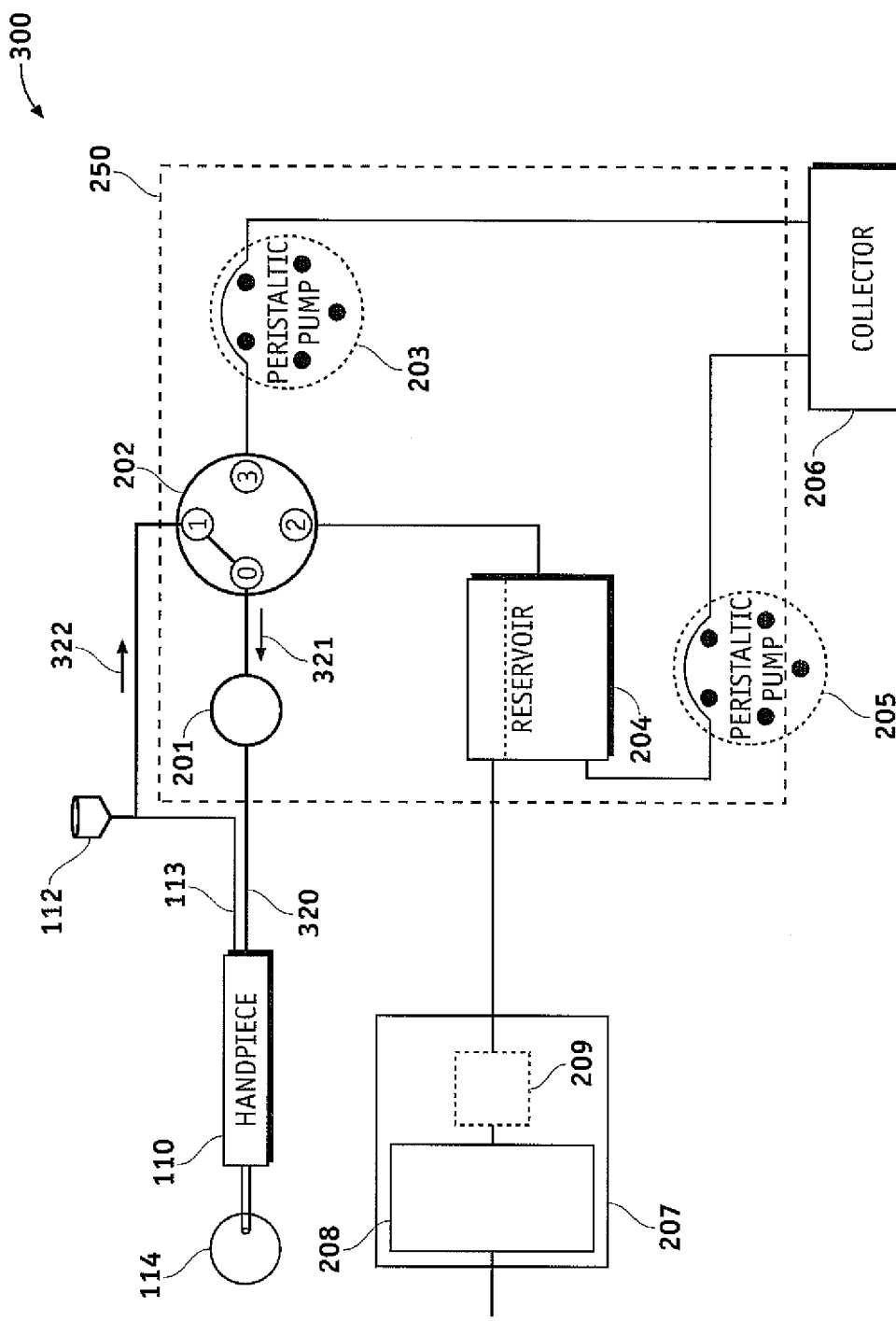
FIG. 3 is a functional block diagram illustrating a surgical cassette venting system configured for venting to a BSS (irrigation) bottle, according to one embodiment of the invention.

FIG. 3 is a functional block diagram illustrating a surgical cassette system configured for venting using a balanced saline solution (BSS) bottle in accordance with an aspect of the present design.

In the arrangement where the flow selector valve 202 connects handpiece 110 with BSS bottle 112, the present design may allow for venting of fluid to eye 114 directly from BSS bottle 112 and/or the line between flow selector valve 202 and BSS bottle 112, where fluid from BSS bottle 112 and/or the line flows toward and through flow selector valve 202. The fluid flow continues to flow toward and through flow selector valve 202 in the direction indicated by arrow 321. In order to vent from BSS bottle 112, instrument host 102 may signal flow selector valve 202 to connect port '0' to port '1'. When the flow selector valve 202 switches to position '1,' fluid may flow from BSS bottle 112 and/or the line between BSS bottle 112 and flow selector valve 202 to handpiece 110 as indicated by directional arrows 322 and 321 as shown in FIG. 3. During fluid venting from bottle 112 and/or the line between BSS bottle 112 and flow selector valve 202, the present design may arrange the bottle position at an elevated height relative to the eye 114, thus realizing a positive pressure source.

Figure 4:
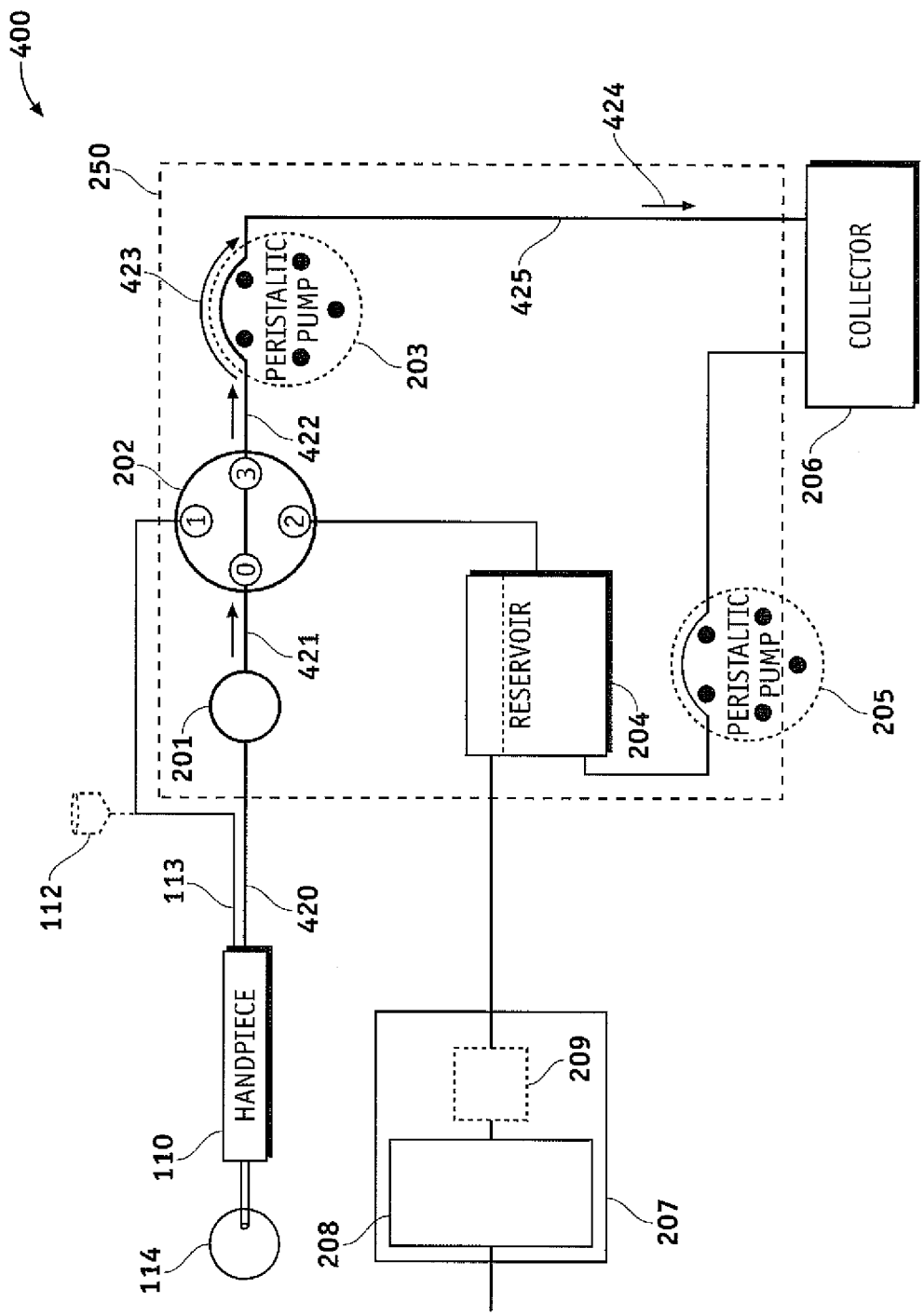
FIG. 4 is a functional block diagram illustrating a surgical cassette venting system configured for peristaltic aspiration operation, according to one embodiment of the invention.

FIG. 4 is a functional block diagram illustrating a surgical cassette system 400 configured for normal peristaltic aspiration. The present design may configure flow selector valve 202 to connect handpiece 110 to pump 203 and may operate selector valve 202 to connect fluid pathway 421 at port '0' to fluid pathway 422 at port '3' of flow selector valve 202. In this aspiration configuration, reservoir 204 is not employed. As pump 203 operates in a clockwise direction to pump fluid in the direction shown by arrow 424, the present design aspirates fluid from eye 114 to collector 206 following the path formed by connecting fluid pathway 420 from the handpiece to fluid vacuum sensor 201, continuing through fluid pathway 421 toward the flow selector valve 202 where a fluid line is connected from flow selector valve 202 to pump 203 and moving fluid in the direction shown by the arrow above fluid pathway 422. Clockwise pump operation shown by arrow 423 forces fluid into fluid pathway 425 in direction 424 toward collector 206. During an ocular procedure, the surgeon may stop the flow of fluid into the eye by stopping pump 203. When pump 203 is stopped, the rollers within the peristaltic pump stop moving and fluid through this path ceases to move or flow.

Figure 5:
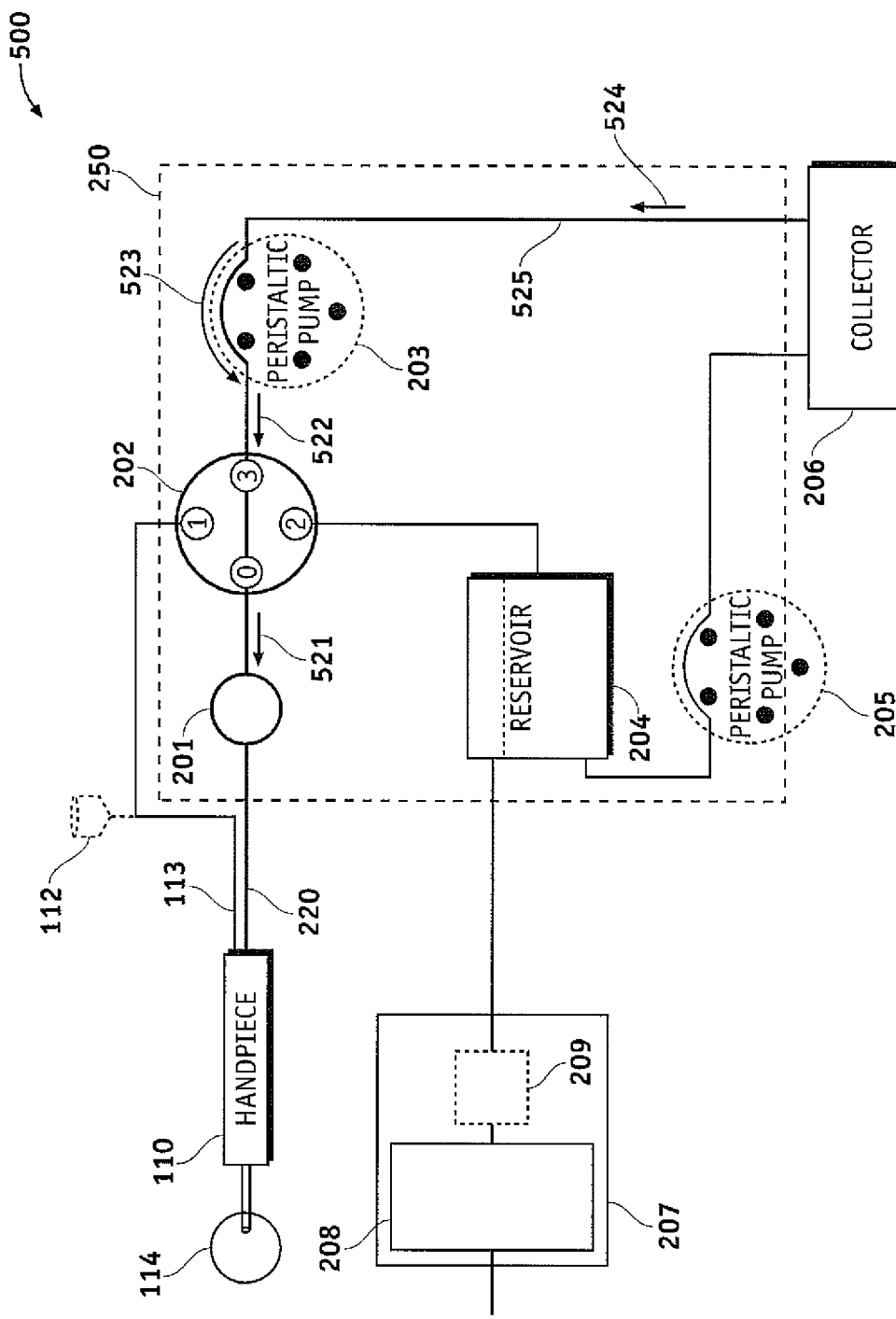
FIG. 5 is a functional block diagram illustrating a surgical cassette venting system configured for peristaltic venting operation, according to one embodiment of the invention.

FIG. 5 illustrates a surgical cassette system 500 configured for venting and reflux operation. The present design may configure flow selector valve 202 to connect handpiece 110 to pump 203 from port '3' to port '0'. As the pump 203 operates in a counter-clockwise direction as shown by arrow 523, the present design may vent fluid through fluid pathway 525 in direction of flow arrows at 524, 523, 522, and 521 and ultimately to fluid pathway 220. Note that in both FIGS. 4 and 5, flow selector valve 202 neither operates to take fluid from nor output fluid to reservoir 204.

In the configuration of FIG. 5, the system can stop the inflow of fluid from fluid pathway 525 to the eye by stopping pump 203 or closing flow selector valve 202, or both. The internal volume of fluid pathway 525 has sufficient fluid volume to provide venting and/or reflux.

Figure 6:
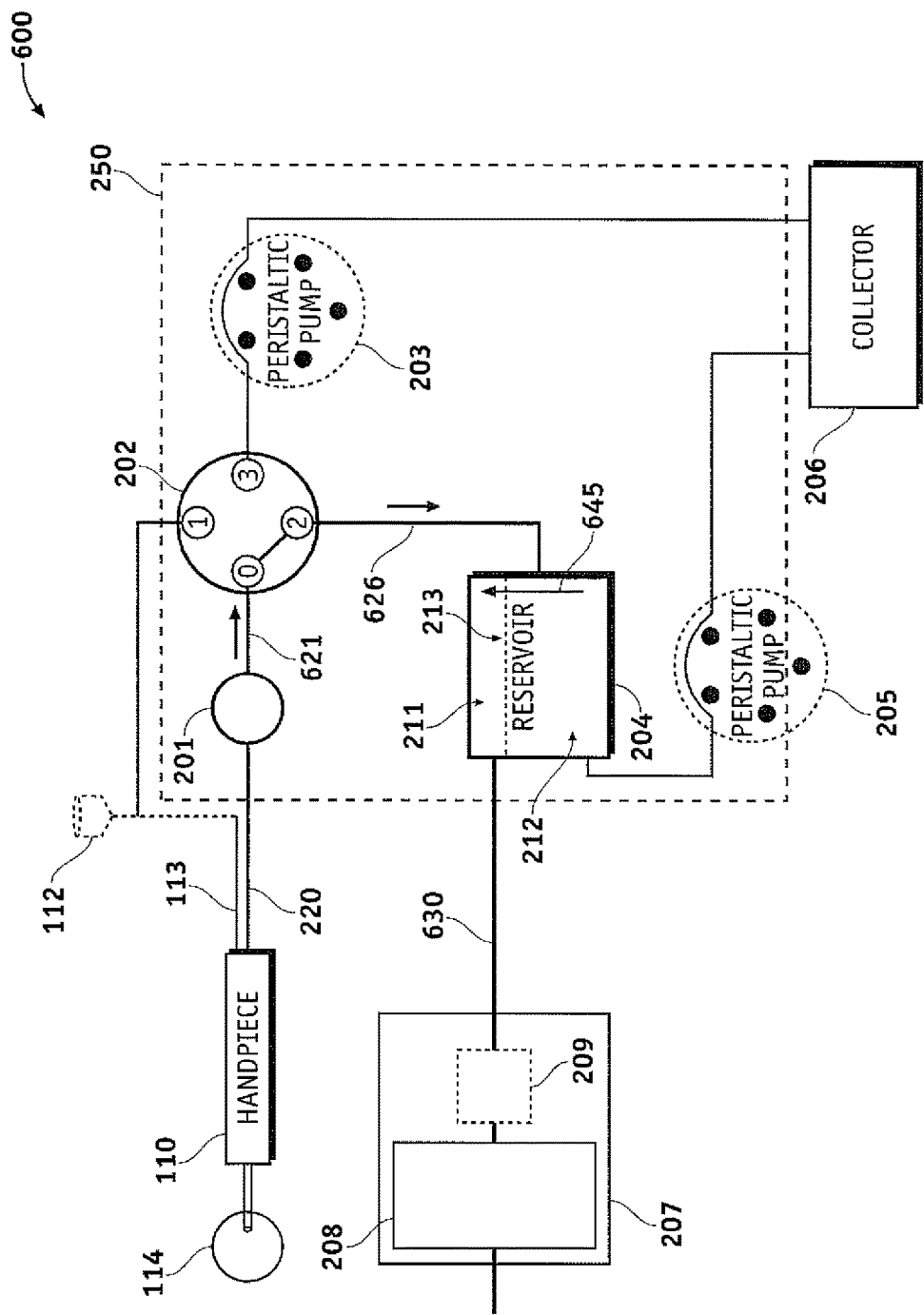
FIG. 6 is a functional block diagram illustrating a surgical cassette venting system configured for vacuum regulator aspiration operation, according to one embodiment of the invention.
Figure 7:
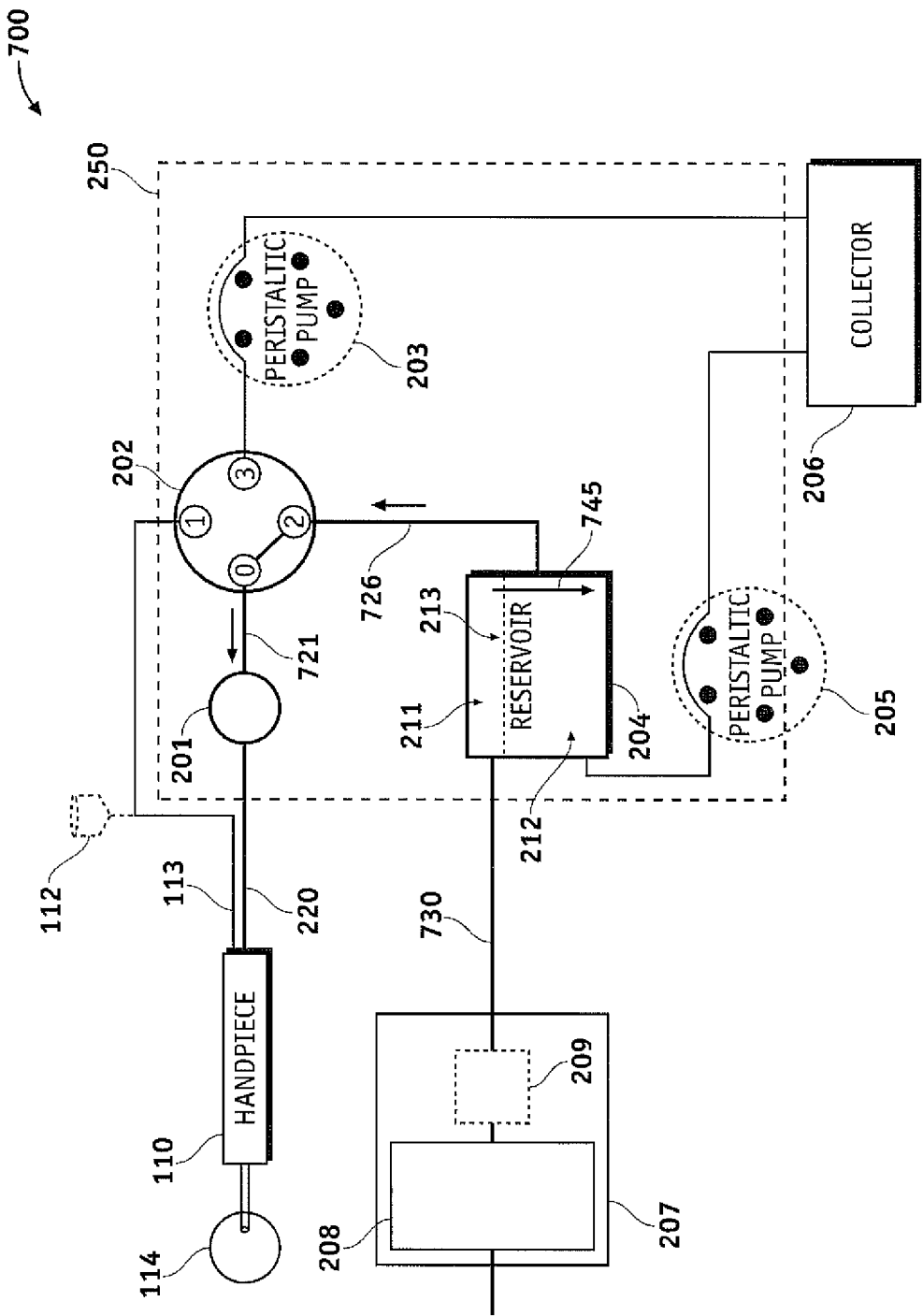
FIG. 7 is a functional block diagram illustrating a surgical cassette venting system configured for vacuum regulator venting operation, according to one embodiment of the invention.

The present design may alternately employ vacuum pump arrangement 207 to aspirate fluid from eye 114 to reservoir 204 as illustrated in FIG. 6, or applying pressure thus forcing fluid from reservoir 204 through selector valve 202 and irrigating eye 114 as illustrated in FIG. 7.

FIG. 6 is a functional block diagram illustrating the system configured for vacuum pump arrangement 207 aspiration operation where the present design may operate either in a normal venturi aspiration mode to create a vacuum at fluid pathway 626. Again, flow selector valve 202 connects handpiece 110 with reservoir 204 from port '2' to port '0'. In this aspiration configuration, pump 203 is not in use and typically not operating. Vacuum pump arrangement 207 may operate to allow pressure to be removed from reservoir 204 either by venting to atmosphere or drawing a vacuum. Removing or reducing pressure using vacuum pump arrangement 207 may move air-fluid boundary 213 upward at 645 to aspirate fluid from eye 114 to reservoir 204. Again, vacuum pump arrangement 207 may include or be attached to a venturi pump or pumping device. The fluid path from eye 114 to reservoir 204 follows the direction indicated by the arrows above fluid passageway 621 and to the right of fluid passageway 626. Optionally, to vent and/or reflux, pressure regulator 209 may be used to increase the pressure in reservoir 204 to cause fluid to flow through fluid pathway 626 toward handpiece 110 via flow selector valve 202.

FIG. 7 is a functional block diagram illustrating a surgical cassette system 700 configured for venting and/or reflux operation in accordance with an aspect of the present invention. The present design may configure flow selector valve 202 to connect handpiece 110 with reservoir 204 from port '2' to port '0'. Vacuum pump arrangement 207 may operate to provide pressure to reservoir 204 via pressure regulator 209. Applying or increasing pressure using pressure regular 209 of vacuum pump arrangement 207 may move air-fluid boundary 213 downward in the direction of 745 causing fluid to flow from reservoir 204 and/or fluid pathway 726 to eye 114.

In sum, the present design surgical cassette system provides for aspiration, venting, and/or reflux using pumping operations. A plurality of pumps are typically employed, including a first pump and a second pump, where a first pump may be pump 203, shown as a peristaltic pump in FIG. 2B, and pump 208, representing a venturi pump in certain embodiments shown herein.

The instrument host 102 may provide a signal to position or switch flow selector valve 202 for desired peristaltic or vacuum regulated operation. Aspiration, venting, and/or reflux may be controlled in various ways, including but not limited to switching offered to the surgeon on the instrument host 102, switching via a switch such as one provided on handpiece 110 or via a footswitch, or via automatic or semi-automatic operation, wherein pressure is sensed at some point, such as coming from the handpiece to the instrument host at sensor 201 or separately sensed by a sensor placed in the ocular region with pressure signals being provided to the instrument host 102. In general, automatic or semi-automatic operation entails sensing a drop or rise in pressure and either aspirating fluid to or venting fluid from the ocular region or eye 114. In any circumstance, the surgeon or other personnel are provided with the ability to run the pumps in any available direction, such as for cleaning purposes.

Other pumping states may be provided as discussed herein and based on the desires of personnel performing the surgical procedure. For example, in the case of the surgeon desiring aspiration operation as shown in FIG. 6 in all circumstances as opposed to aspiration as shown in FIG. 4, the surgeon may enable settings or the instrument host may provide for the surgeon to select such operation. Additionally, if the surgeon believes venturi pumping or vacuum regulator operation should be employed wherever possible, she may select that from the instrument host. Other configurations may be provided, including limiting ocular pressure within a desired range, and so forth.

Certain additional functionality or components may be provided in the current design. For example, a valve (not shown) may be located between pump 203 and flow selector valve 202 or between pump 203 and handpiece 110 in the design, such as in the design of FIG. 3, to build a bolus of fluid or build pressure between the valve and pump 203. Such a valve can thereby create positive pressure when pump 203, such as a peristaltic pump, reverses direction of flow and provides pressure to the valve. This positive pressure can be released by opening the valve thereby venting the system.

Referring to FIG. 1, the instrument host 102 will generally include at least one processor for processing instructions and sending command signals to other components of the system, and memory for storing instructions. The instrument host 102 and GUI host may be housed in a console. The instructions generally include methods for operating the system 100. Methods disclosed herein may be stored as instructions on the memory.

Figure 8:
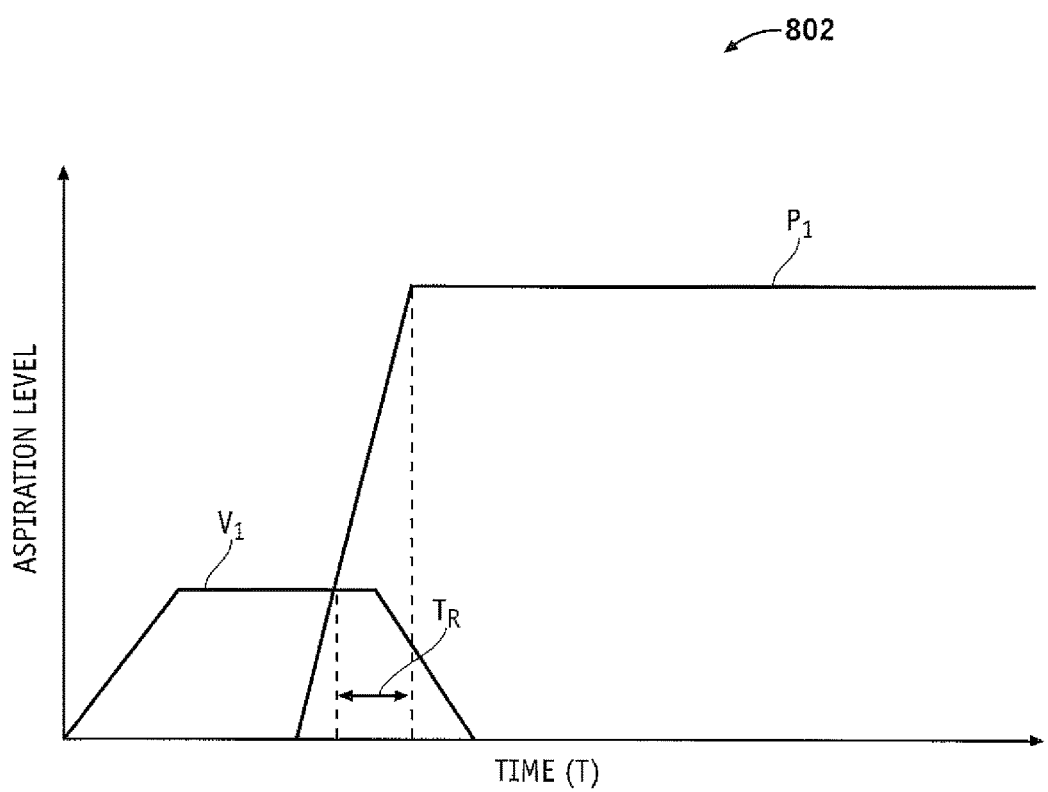
FIG. 8 is a graphical depiction of the operation of a surgical system, according to one embodiment of the invention.

FIG. 8 shows a graph 802 which depicts a system switching from a first pump to a second pump according to one embodiment of the invention. The system may be the system 100 depicted in FIG. 1. Curve $V_I$ shows the operation of the first pump in terms of aspiration level (which may be flow-rate or vacuum level) versus time T. The first pump may be a volumetric, e.g. peristaltic or other displacement, pump. The first pump is capable of attaining a limited aspiration level, as shown. Curve $P_I$ shows the operation of the second pump in terms of aspiration level versus time T. The second pump may be a pressure, e.g. venturi or other pressure differential, pump and capable of a higher aspiration level than the first pump. As shown, through cassette arrangement 250, the second pump may begin operation while the first pump is operating at its maximum aspiration level, and thus a transitional time $T_R$ between the peak aspiration levels is constantly increasing. Note that the time for initiating of a newly energized pump may occur before, during, or after a start time of the ramp-down or decreasing of aspiration flow from a previously operating pump. Similarly, a complete halt of flow or end of the ramp-down may occur before, during or after the end of the ramp-up, so that the transitions shown schematically herein are simplified. Also, the ramp-up and ramp-down of aspiration may more accurately be represented by curves (rather than single linear slopes). Nonetheless, the ramp-up of the newly employed pump (the second pump) will typically start before the ramp-down of the first pump has been completed. Thus, there is typically no time delay between switching of the pumps. Automatic switching between pumping systems, without the need for user interaction may be applied by automated control of the flow selector valve 202. Switching may occur as a series of cycles or pulses, and thus occur over a very short period of time, in some examples having a frequency of a few milliseconds, less than a second, and/or a few seconds. A user may preprogram how and/or when switching between multiple pumps occurs.

Figure 9A:
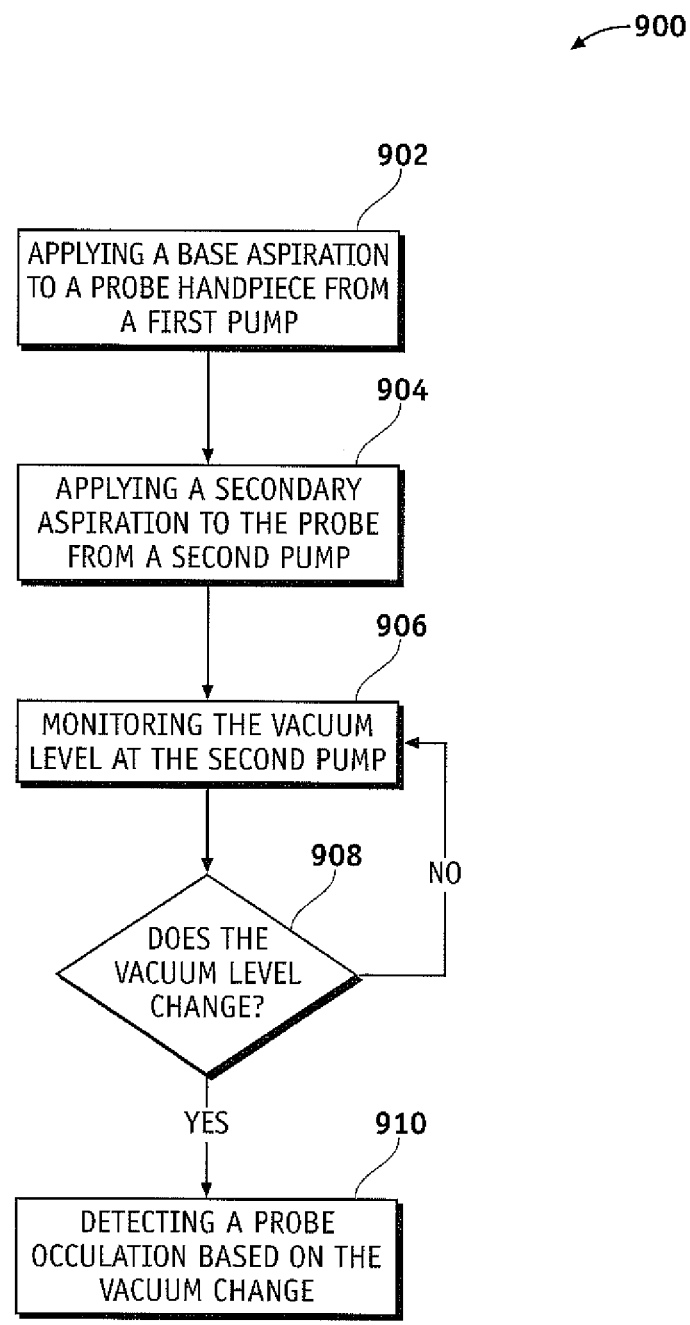
FIG. 9A is a flow chart of a method for applying aspiration to a probe, according to one embodiment of the invention.

FIG. 9A shows a method 900 for applying aspiration to an eye using a probe (e.g. handpiece), according to one embodiment of the invention. Method 900 may be employed on the system 100 shown in FIG. 1. When solely using a pressure pump (e.g. a venturi/vacuum-type pump) to aspirate an eye, it may be difficult to detect when the probe is occluded by sensing vacuum changes when using a pressure pump. This is because the pressure pump may be configured to automatically compensate for pressure level, and thus no detectable pressure change is available. Method 900 tracks pressure changes from a secondary pump, which may be a volumetric pump, to detect occlusions while in a high flow-rate aspiration mode. At operation 902 a first pump, operating at a high flow-rate (e.g. high vacuum-rate), aspirates via a probe which is in a region of an eye. The probe for example may be a phacoemulsification device or a vitrectomy device. The first pump may be a pressure, e.g. venturi, pump. At operation 904 a second pump, operating at a low-flow rate, also aspirates via the probe. The second pump may be a volumetric pump, e.g. a peristaltic pump. At operation 906 the vacuum level, or pressure differential, of the second pump is monitored. As shown in operation 908, if a vacuum change is not detected via a pressure sensor or similar device, then the vacuum level is continuously monitored. If a vacuum change is detected, for example by an increased pressure differential above a base pressure differential, then the probe may be determined to be at least partially occluded and thus in contact with cataract tissue, as shown in operation 910. Detection of the occlusion-induced pressure change may be facilitated by altering or inhibiting operation of the pressure-regulating system of the venturi pump in some modes, such as by the use of a check valve to avoid reflux flow from the venturi pump toward the pressure sensor of the cassette.

Phacoemulsification probes often work optimally when sufficiently occluded, as the ultrasonically energized tip will then be engaged with the tissue targeted for fragmentation. Thus, the determination that the probe is at least partially occluded may follow with an application of, change and/or adjustment of ultrasonic energy to the probe. Additionally, the first pump may be instructed to be switched off, so that aspiration is performed by the second pump only.

Figure 9B:
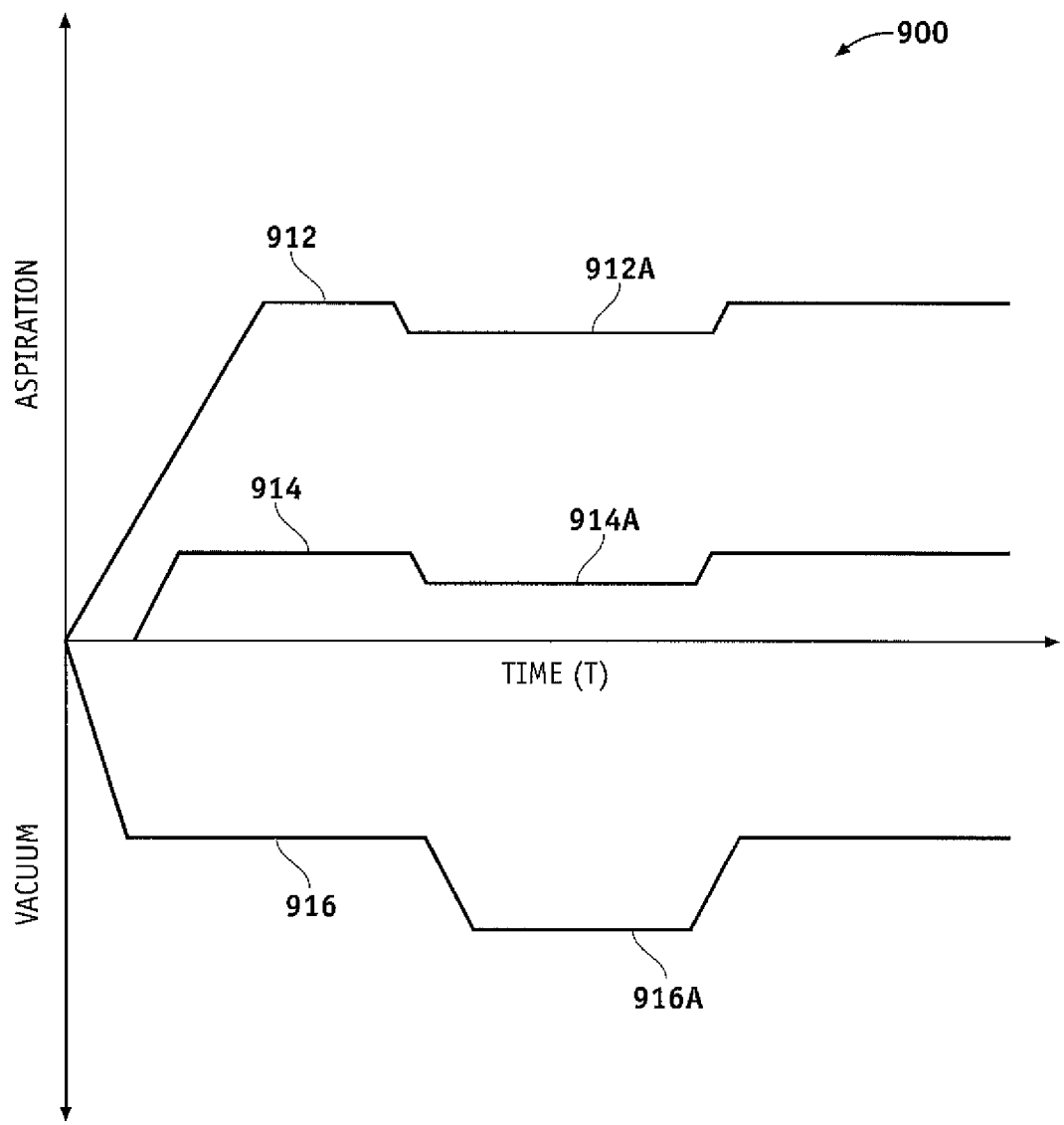
FIG. 9B is a graphical depiction of the operation of a surgical system, according to one embodiment of the invention.

FIG. 9B shows a graphical depiction of method 900 shown in FIG. 9A, according to one embodiment of the invention. Curves 912 and 914 show the aspiration flows of the first pump and second pump, respectively. Curve 916 shows the pressure differential, which is detected from the second pump, which may be a peristaltic pump. Curve dips 912A and 914A indicate that the probe has been at least partially occluded, resulting in a reduced aspiration rate. Simultaneously, an increased pressure differential, shown by curve increase 916A, shows a detectable response. Accordingly, the increase pressure differential may be used to send command signals to various portions of the system.

Figure 10A:
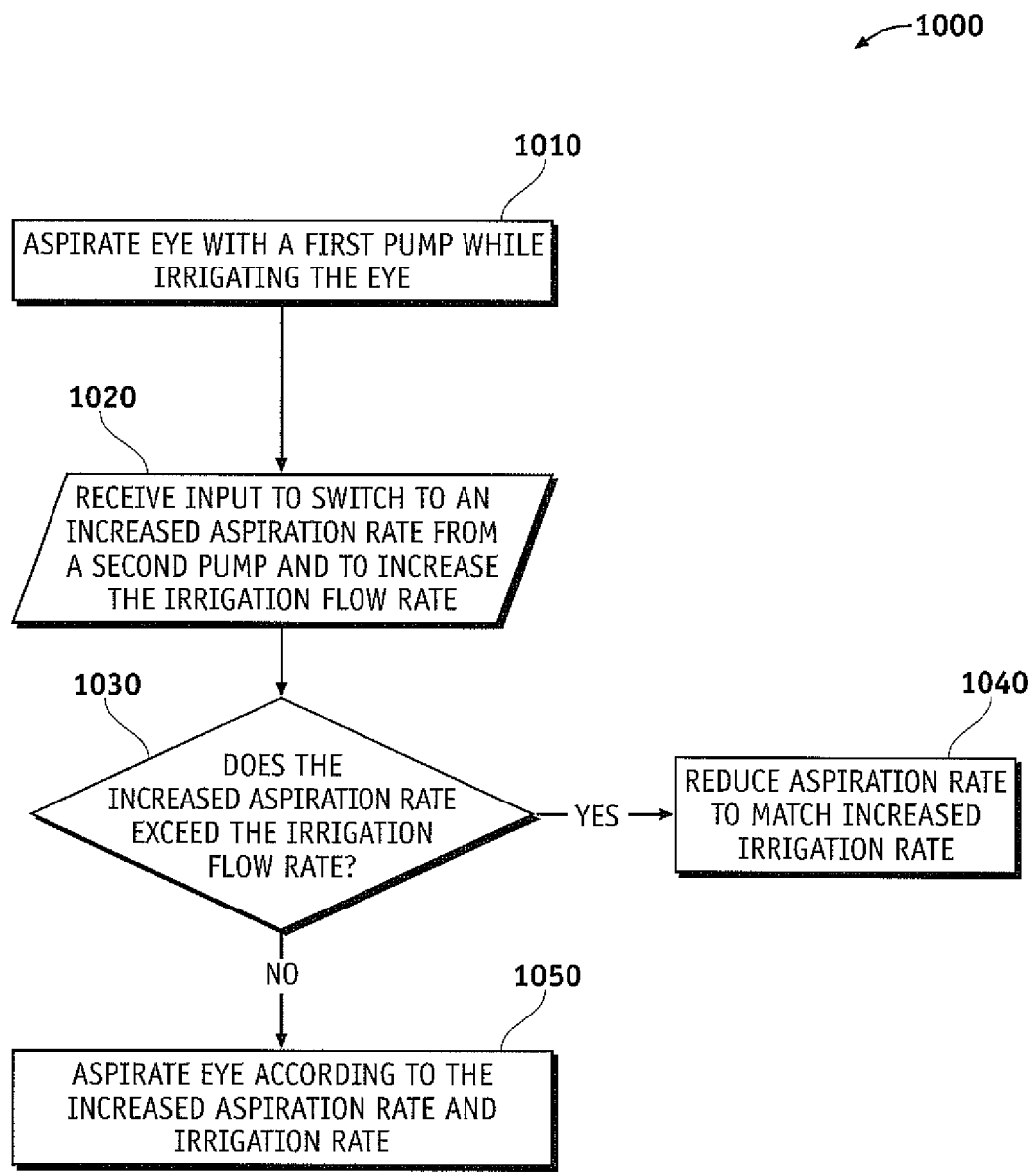
FIG. 10A is a flow chart of a method for applying aspiration and irrigation to a probe, according to one embodiment of the invention.

FIG. 10A shows a method 1000 for applying aspiration to an eye using a probe, according to one embodiment of the invention. Method 1000 may be employed on the system 100 shown in FIG. 1. At operation 1010 a first pump, operating at a low flow-rate, aspirates via a probe which is in a region of an eye. The first pump may be a volumetric, e.g. peristaltic, pump. Additionally, irrigation is also being supplied to the eye using the probe. Irrigation may be provided, for example by irrigation fluid source 112. At operation 1020 an input is received to switch to a second pump, and increase the aspiration via the probe and also to increase irrigation. The second pump may be a pressure pump (e.g. venturi pump). The signal may be automatically triggered by a command signal generated in response to a detected condition, for example by detecting that the probe is not sufficient occluded to provide ultrasonic energy to cataract tissue (often per pressure signals generated along the aspiration pathway). The signal may also be manually triggered by a user input, for example through the actuation of a foot switch. Various means may be employed to increase the irrigation rate, for example a fluid source may be automatically placed at a higher position and/or pressurized infusion may be used. An example of this is shown in co-assigned U.S. patent application Ser. No. 11/937,640, the entirety of which is incorporated by reference herein. The fluid source may also be a bagged fluid source and additional pressure, externally or internally, may be automatically applied to increase the irrigation rate. Examples of this are shown in U.S. Pat. No. 6,491,661, the entirety of which is incorporated by reference herein. Additionally, some examples of factors which should be taken into consideration when supplying automatic irrigation are phacoemulsification device tip size, and surgical technique. These factors may be inputted into the console for consideration by the processor. Thus, fluidic settings (vacuum, aspiration levels) can be limited based on the irrigation level, tip gage, and surgical technique. At operation 1030 it is determined if whether the increased aspiration rate will exceed the maximum irrigation rate, which would be an undesirable condition as the eye may be removed of all fluid. At operation 1040, if the increased aspiration rate exceeds the maximum irrigation rate, then the aspiration rate will be automatically decreased to match the irrigation rate, resulting in a balanced fluid supply condition in the eye. At operation 1050, if the increased aspiration rate does not exceed the maximum irrigation rate, then the aspiration and irrigation rates will increase according to the input of operation 1020. Additionally, if the system detects that the probe has been occluded, resulting in decreased aspiration, the irrigation rate may be reduced automatically to match.

Figure 10B:
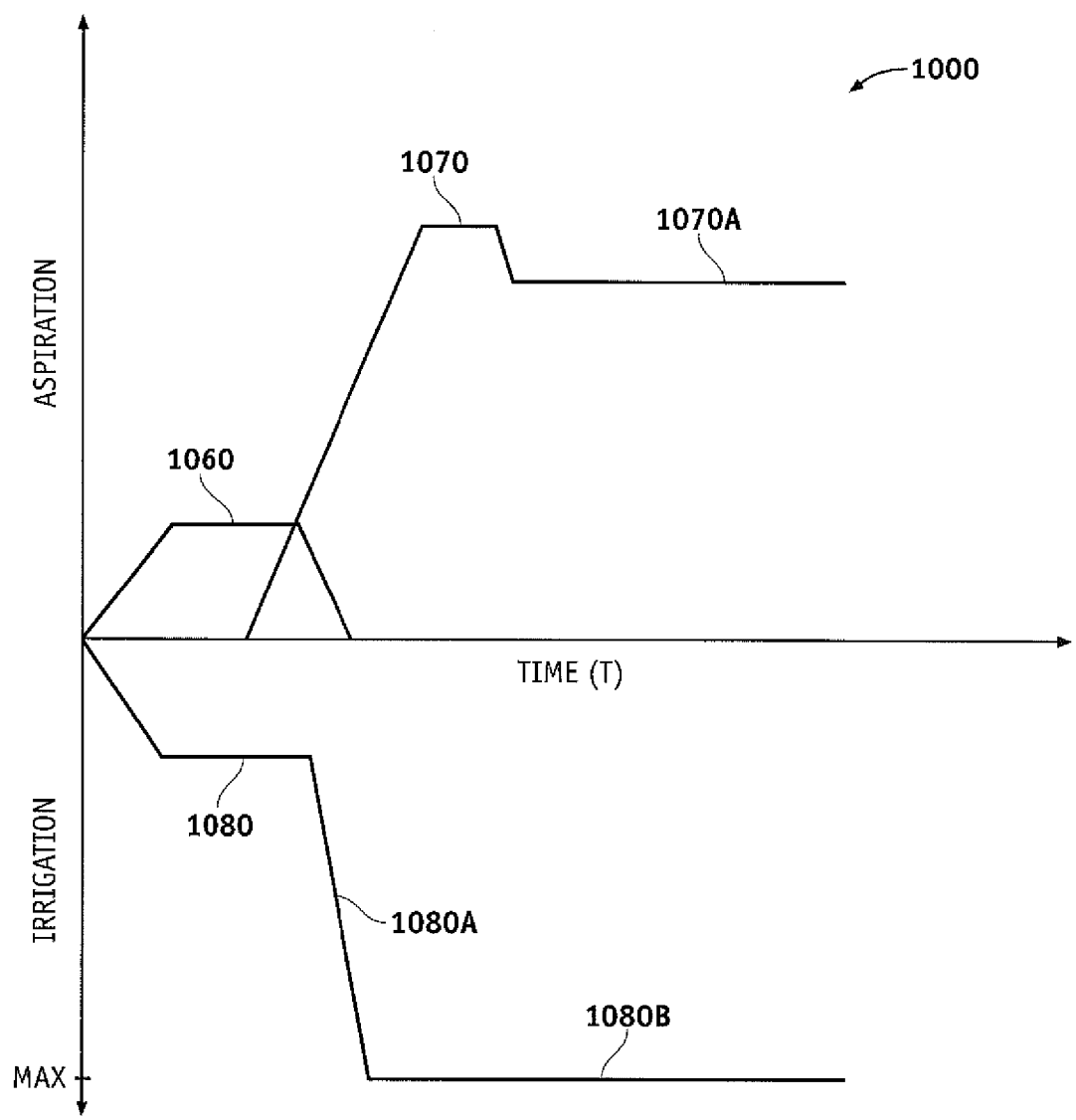
FIG. 10B is a graphical depiction of the operation of a surgical system, according to one embodiment of the invention.

FIG. 10B shows a graphical depiction of method 1000, shown in FIG. 10A, according to one embodiment of the invention. Curves 1060 and 1070 show the aspiration flows of the first pump and second pump, respectively. Curve 1080 shows the irrigation flow rate supplied to the probe. At curve portion 1080A the irrigation flow rate is increased to match the increased aspiration rate of the second pump. At curve portion 1080B, the irrigation flow rate is shown at its maximum possible flow rate. Curve portion 1070 shows that the maximum aspiration rate has exceeded the maximum irrigation rate, and thus the aspiration rate is automatically decreased to compensate, as shown in curve portion 1070A.

Figure 11A:
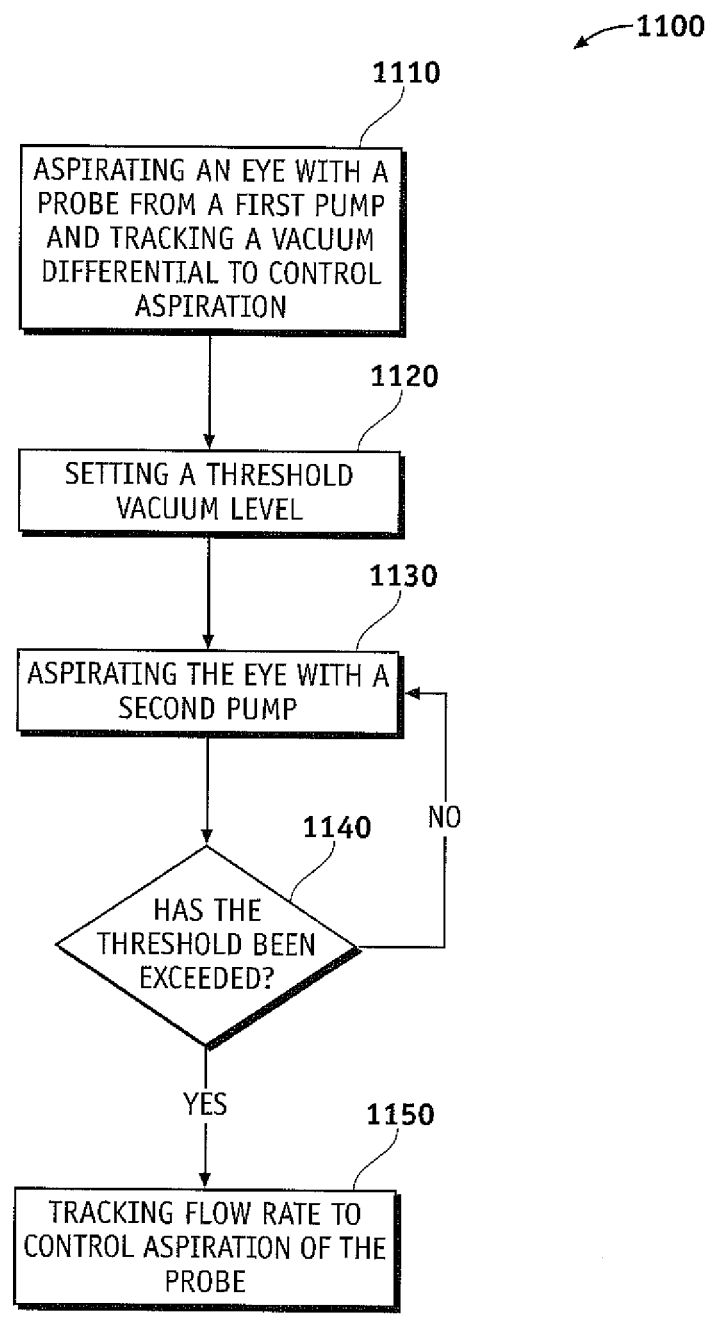
FIG. 11A is a flow chart of a method for applying aspiration to a probe, according to one embodiment of the invention.

FIG. 11A shows a method 1100 for applying aspiration to an eye using a probe, according to one embodiment of the invention. Method 1100 may be employed on system 100 shown in FIG. 1. In some dual-pump systems, tracking vacuum level for control feedback means does not apply in equivalent terms to each pump. For example, 500 mmHg of vacuum detected during the operation of a peristaltic pump may result in an aspiration rate which is far lower than that for 500 mmHg detected during the operation of a venturi pump. Accordingly, using the same measurement for control feed back for each pump may result in a dangerous condition, e.g. the eye running out of fluid and chamber collapse. At operation 1110 a first pump, operating at a low flow-rate, aspirates through a probe which is in a region of an eye. The first pump may be a volumetric, e.g. peristaltic, pump. The vacuum created by the aspiration is tracked to provide feed back control aspects of the probe operation and aspiration. At operation 1120 a threshold is set for a maximum vacuum level which is used for feedback control purposes. Although only one threshold is shown, there may be multiple thresholds set for one, two, or both pumps. At operation 1130, aspiration through the probe is switched to a second pump, which increases the aspiration rate to the probe. The second pump may be a pressure pump (e.g. venturi pump). At operation 1140 it is determined whether the threshold has been passed. If the threshold has not been passed, then the method 1100 loops back to operation 1130. If the threshold has been passed, the system switches to control the probe based on flow rate, which may be calculated from known and measured quantities, some examples including tip size, type of procedure, irrigation flow rate, pressure differentials, and actual flow rate. The same flow rate should be at least initially matched when switching between pumps. Multiple thresholds may be programmed for one or more pumps and/or thresholds may be programmed for a combination of pumps. However, measuring flow rate from a flow meter may be difficult because of the interaction of cataract particles with a flow meter.

Figure 11B:
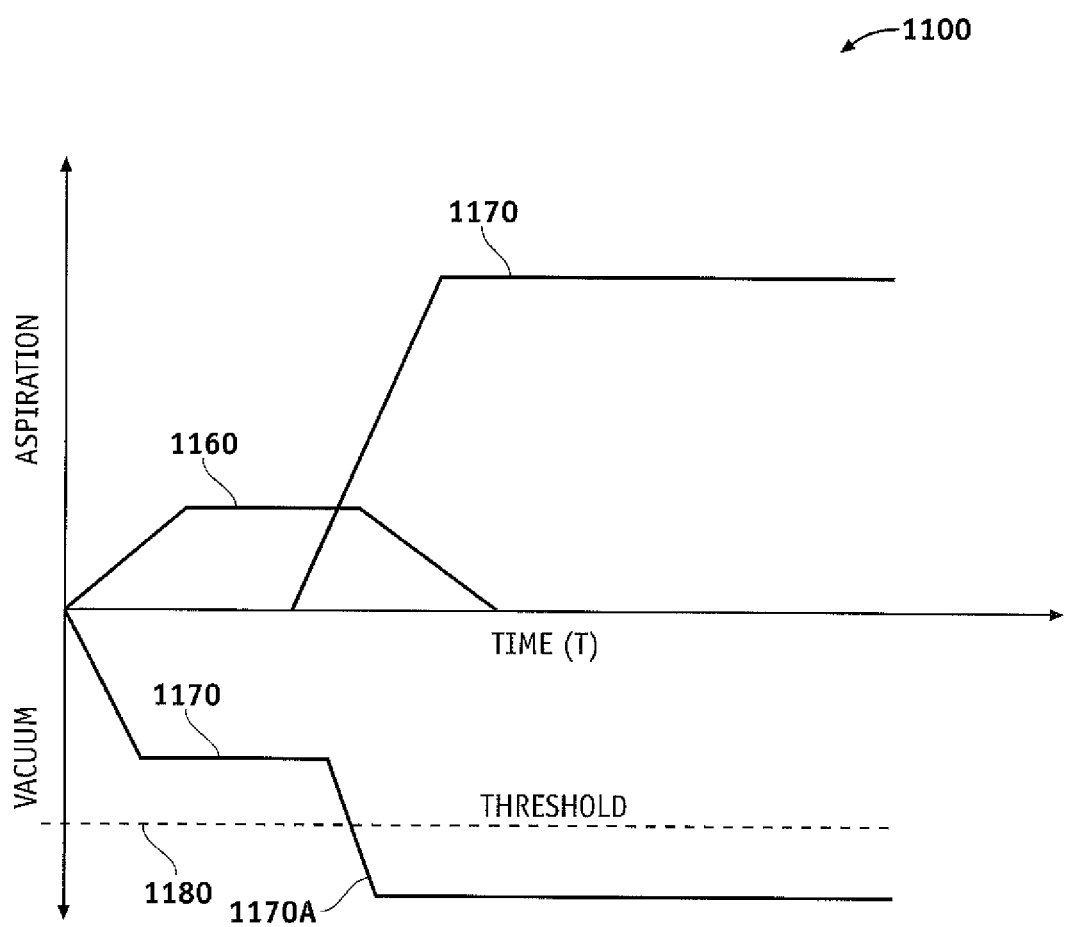
FIG. 11B is a graphical depiction of the operation of a surgical system, according to one embodiment of the invention.

FIG. 11B shows a graphical depiction of method 1100, shown in FIG. 11A, according to one embodiment of the invention. Curves 1160 and 1170 show the aspiration flows of the first pump and second pump, respectively. Curve portion 1190 shows the vacuum being tracked for control feedback of the probe. Dotted line 1180 shows the threshold vacuum level. Curve portion 1190A shows that the threshold has been passed, and accordingly the system will switch from vacuum feedback based controls to flow-rate based controls.

The methods and devices disclosed herein may also be used utilized with co-assigned and concurrently filed U.S. Provisional Patent Application No. 61/198,658, entitled AUTOMATICALLY PULSING DIFFERENT ASPIRATION LEVELS TO AN OCULAR PROBE, which is incorporated by reference herein in its entirety.

It should be noted that the examples disclosed herein may describe low-flow rate pumps as peristaltic pumps, and high flow-rate pumps as venturi pumps. These are merely examples and are not limiting to the embodiments disclosed herein, for example high-flow rate peristaltic pumps may be used in lieu of high flow-rate venturi pumps, and low flow-rate venturi pumps may be used in lieu of low-flow rate pumps peristaltic pumps. Additionally, a low flow-rate venturi pump may be used in conjunction with a high flow-rate venturi pump, and a low flow-rate peristaltic pump may be used in conjunction with a high flow-rate peristaltic pump.

As will be understood by those skilled in the art, the present invention may be embodied in other specific forms without departing from the essential characteristics thereof. Those skilled in the art will recognize, or be able to ascertain using no more than routine experimentation, many equivalents to the specific embodiments of the invention described herein. Such equivalents are intended to be encompassed by the following claims.

What is claimed is:

1. A system for removing material from within an eye, the system comprising:
    a probe having a distal tip insertable into the eye, wherein the distal tip comprises an aspiration port;
    a console coupled with the aspiration port along an aspiration pathway, wherein the console comprises a processor and a pump system for providing a first pump rate via a first pump and a second pump rate via a second pump that is higher than the first pump rate; and
    wherein the processor is configured to automatically switch from the first pump rate to the second pump rate, to begin a ramp-up of the second pump before a ramp-down of the first pump such that a flow rate while providing the first pump rate is matched to a flow rate when switching from the first pump rate to the second pump rate, to control aspiration through the probe by tracking a vacuum level up to a threshold, and to control aspiration through the probe by tracking a flow rate through the probe when the threshold has been passed.

2. The system of claim 1, wherein the probe comprises a phacoemulsification probe.

3. The system of claim 1, wherein the probe comprises a vitrectomy probe.

4. The system of claim 1, wherein the first pump is a peristaltic pump and the second pump is a venturi pump.

5. The system of claim 1, wherein the threshold passes while the second pump rate is provided.

6. A method for removing material from within an eye, the method comprising:
    aspirating an eye with a probe using a first pump at a first pump rate and tracking a vacuum differential to control aspiration through the probe;
    setting a threshold vacuum level;
    automatically switching from the first pump to aspirating the eye with a second pump at a second pump rate higher than the first pump rate, wherein a ramp-up of the second pump starts before a ramp-down of the first pump such that a flow rate during the switch is matched;
    determining that the threshold vacuum level has been passed; and
    controlling aspiration through the probe by tracking a flow rate through the probe, based on determining that the threshold vacuum level has been passed.

7. The method of claim 6, wherein the probe comprises a phacoemulsification probe.

8. The method of claim 6, wherein the probe comprises a vitrectomy probe.

9. The method of claim 6, wherein the first pump is a peristaltic pump and the second pump is a venturi pump.

10. The method of claim 6, wherein the threshold vacuum level passes while the second pump rate is provided.

\* \* \* \* \*